(12) United States Patent
Katragadda et al.

(10) Patent No.: US 12,327,641 B2
(45) Date of Patent: Jun. 10, 2025

(54) SYSTEM AND METHOD FOR PREDICTING WELLNESS METRICS

(71) Applicant: Myelin Foundry Private Limited, Bengaluru (IN)

(72) Inventors: Gopichand Katragadda, Bangalore (IN); Ganesh Suryanarayanan, Bangalore (IN)

(73) Assignee: MYELIN FOUNDRY PRIVATE LIMITED, Bengaluru (IN)

( * ) Notice: Subject to any disclaimer, the term of this patent is extended or adjusted under 35 U.S.C. 154(b) by 286 days.

(21) Appl. No.: 17/594,012

(22) PCT Filed: Jul. 12, 2019

(86) PCT No.: PCT/IN2019/050519
§ 371 (c)(1),
(2) Date: Sep. 30, 2021

(87) PCT Pub. No.: WO2020/202173
PCT Pub. Date: Oct. 8, 2020

(65) Prior Publication Data
US 2022/0157467 A1 May 19, 2022

(30) Foreign Application Priority Data
Apr. 2, 2019 (IN) .............................. 201941013325

(51) Int. Cl.
*G16H 50/30* (2018.01)
*A61B 5/00* (2006.01)
(Continued)

(52) U.S. Cl.
CPC ........... *G16H 50/30* (2018.01); *A61B 5/0088* (2013.01); *A61B 5/02055* (2013.01);
(Continued)

(58) Field of Classification Search
CPC ........ G16H 40/67; G16H 50/30; G16H 50/70; A61B 5/02055; A61B 5/053; A61B 5/14507; A61B 5/14546; A61B 5/7275
(Continued)

(56) References Cited

U.S. PATENT DOCUMENTS

2009/0253968 A1* 10/2009 Cho ........................ A61B 5/318
600/323
2010/0331146 A1   12/2010 Kil
(Continued)

FOREIGN PATENT DOCUMENTS

WO   WO-2011106792 A2 *  9/2011 ........... A61B 5/0059

OTHER PUBLICATIONS

Engman, Zoie; Design and Validation of a Wearable, Continuous, and Non-Invasive Hydration Monitor that Uses Ultrasonic Pulses to Detect Changes in Tissue Hydration Status; California Polytechnic State University, ProQuest Dissertations Publishing, 2014. 30511636 (Year: 2014).*

(Continued)

*Primary Examiner* — Hiep V Nguyen
(74) *Attorney, Agent, or Firm* — IPHORIZONS PLLC; Narendra Reddy Thappeta

(57) ABSTRACT

A method (200) for predicting a wellness metric (208, 314, 612) is presented. The method (200) includes maintaining (202) a model which receives as input a set of parameters and provides as output a wellness metric (208, 314, 612). Furthermore, the method (200) includes receiving (204) a set of non-invasive biological parameters (106, 404, 602) of a user (102). In 5 addition, the method (200) includes providing (206) the set of non-invasive biological parameters (106, 404, 602) as the set of parameters to the model to cause the model to generate a wellness metric (208, 314, 612) for the user (102).

20 Claims, 8 Drawing Sheets

(51) Int. Cl.
   *A61B 5/0205* (2006.01)
   *A61B 5/024* (2006.01)
   *A61B 5/053* (2021.01)
   *A61B 5/145* (2006.01)
   *G16H 40/67* (2018.01)
   *G16H 50/70* (2018.01)

(52) U.S. Cl.
   CPC .......... *A61B 5/02405* (2013.01); *A61B 5/053* (2013.01); *A61B 5/14507* (2013.01); *A61B 5/14546* (2013.01); *A61B 5/449* (2013.01); *A61B 5/7275* (2013.01); *G16H 40/67* (2018.01); *G16H 50/70* (2018.01)

(58) Field of Classification Search
   USPC ............................................................ 705/2
   See application file for complete search history.

(56) References Cited

U.S. PATENT DOCUMENTS

| | | | |
|---|---|---|---|
| 2011/0152646 A1* | 6/2011 | Anderson | A61B 5/1459 600/309 |
| 2011/0172545 A1* | 7/2011 | Grudic | G16H 50/50 600/485 |
| 2012/0321759 A1* | 12/2012 | Marinkovich | A61B 5/442 356/402 |
| 2014/0107433 A1 | 4/2014 | Wegerich | |
| 2014/0180037 A1* | 6/2014 | Zhang | A61B 5/14551 600/301 |
| 2015/0112158 A1 | 4/2015 | He et al. | |
| 2015/0112170 A1* | 4/2015 | Amerson, III | A61B 5/14532 600/316 |
| 2016/0239624 A1 | 8/2016 | Short et al. | |
| 2019/0076031 A1 | 3/2019 | Valys et al. | |

OTHER PUBLICATIONS

International Search Report and Written Opinion issued by the International Searching Authority for Application No. PCT/IN2019/050519, dated Jan. 29, 2020, 08 pages.

Office Action for India Appl. No. 201941013325, dated Jul. 30, 2019, 10 pages.

* cited by examiner

SYSTEM AND METHOD FOR PREDICTING WELLNESS METRICS

CROSS REFERENCE TO RELATED APPLICATION

This patent application is the U.S. national stage application under 35 U.S.C § 371 of International Patent Application No. PCT/IN2019/050519, filed on Jul. 12, 2019, which claims priority from the Indian Provisional Patent Application Serial No. 201941013325, filed 2 Apr. 2019, titled "SYSTEM AND METHOD FOR PREDICTING WELLNESS MEASURES" the entire disclosure of which is incorporated herein by reference.

BACKGROUND

Embodiments of the present specification relate generally to wellness, and more particularly to systems and methods for predicting one or more wellness metrics corresponding to an object of interest such as a user.

Wellness is typically defined as a state or quality of being in good health and an absence of illness. In the recent years, there has been a discernable and urgent need for shifting the focus of the healthcare system from "diagnose and cure" to "predict and prevent," thereby encouraging pre-emptive action. Hence, there is a growing need for measuring wellness of a user population to proactively galvanize desired preventive actions or measures.

Moreover, there exists a strong connection between wellness and physical health outcomes of a user. Stress is defined as a state of a human body in which a steady state is disturbed as a result of various external and internal stressors, resulting in emotional and/or physical tension. Some common sources of stress include lifestyle, poor dietary habits, lack of sleep, lack of exercise, environmental factors, injury, or an infection. A commonly occurring manifestation of the body's reaction to stress is inflammation.

It may be noted that inflammation is an essential part of the response of the body's immune system to stress, injury, infection, and the like. Inflammation serves as an indication to the immune system to heal and repair any damaged tissue and/or defend the body against infections caused by viruses and bacteria. It is desirable to treat any inflammation in a timely manner to minimize any adverse impact on the health of the person/user. If symptoms of inflammation exist for a relatively short period of time, the condition is generally referred to as acute inflammation. However, if the symptoms persist, the acute inflammation may turn into chronic inflammation. Chronic inflammation is a prolonged condition in which inflammation, tissue injury, and attempts to repair co-exist, however with no resolution. Moreover, chronic inflammation has also been linked to heart disease, stroke, obesity, diabetes, chronic kidney disease, Alzheimer's, cancer, and autoimmune disorders, such as rheumatoid arthritis and lupus.

Currently available techniques for identifying inflammation call for the use of markers, where the markers are determined via tests that entail invasively obtaining samples such as blood and tissue from the user, collecting samples of saliva and/or urine from the user, and the like. More particularly, these samples need to be processed in a laboratory or other clinical settings to determine the markers. Some examples of the markers include C-reactive protein (CRP), salivary cortisol, serum protein electrophoresis (SPEP or SPE), and the like. These markers are used to facilitate medical analytics such as diagnosis, treatment planning, and the like. However, determination of these markers suffers from numerous shortcomings. For example, determining the markers entails invasively drawing a sample from the user, which may disadvantageously result in additional stress to the user. Further, the additional stress experienced by the user may detrimentally lead to false positive results.

Presently, there exist a limited number of traditional methods and/or other approaches to measure wellness. However, these methods/approaches use a pre-determined set of physiological parameters and biological models to measure wellness. Consequently, the currently available approaches are restrictive in nature since the techniques are tied down to a predetermined biological model and/or biological relationships.

Moreover, in recent times, machine learning techniques have been used extensively in various fields such as medical imaging, diagnostics, and analytics. Specifically, the field of diagnostics and analytics have immensely benefitted by the infusion of deep learning techniques. Use of the deep learning techniques have led to advancements in the state-of-the-art in a myriad of diagnostic and/or analytics tasks. However, currently, while machine learning techniques have shown promise in diagnostic methods in imaging modalities such as computed tomography (CT) and magnetic resonance imaging (MRI), use of machine learning techniques for measuring wellness has not been explored heretofore.

BRIEF DESCRIPTION

In accordance with aspects of the present specification, a method for predicting a wellness metric is presented. The method includes maintaining a model which receives as input a set of parameters and provides as output a wellness metric. Furthermore, the model includes receiving a set of non-invasive biological parameters of a user. In addition, the method includes providing the set of non-invasive biological parameters as the set of parameters to the model to cause the model to generate a wellness metric for the user. Moreover, a non-transitory computer readable medium that stores instructions executable by one or more processors to perform the method for predicting a wellness metric is also presented.

In accordance with another aspect of the present specification, another method for predicting a wellness metric corresponding to a user is presented. The method includes receiving a set of non-invasive parameters corresponding to the user. Furthermore, the method includes receiving an input corresponding to one or more selected tasks. In addition, the method includes retrieving at least one task-specific model corresponding to the one or more selected tasks based on the input. The method also includes predicting an outcome based on the set of non-invasive parameters and the task-specific model, where the outcome corresponds to the wellness metric, predicted values of one or more invasive parameters, or both the wellness metric and the predicted values of the one or more invasive parameters, and where the wellness metric is representative of a quantified biological parameter corresponding to the user. Moreover, the method includes providing the outcome to facilitate analysis.

In accordance with yet another aspect of the present specification, a system for predicting a wellness metric corresponding to a user is presented. The system includes an acquisition subsystem configured to obtain a set of non-invasive parameters corresponding to the user. Moreover, the system includes a processing subsystem in operative association with the acquisition subsystem and including a prediction platform, where the prediction platform is configured to receive a set of non-invasive parameters corresponding to the user, receive an input corresponding to one or more selected tasks, retrieve at least one task-specific model corresponding to the one or more selected tasks based on the input, and predict an outcome based on the set of non-invasive parameters and the task-specific model, where the outcome corresponds to the wellness metric, predicted values of one or more invasive parameters, or both the wellness metric and the predicted values of the one or more invasive parameters, and where the wellness metric is representative of a quantified biological parameter corresponding to the user. Furthermore, the system includes an interface unit configured to provide the outcome to facilitate analysis.

In accordance with another aspect of the present specification, a processing system for predicting a wellness metric corresponding to a user is presented. The processing system includes a prediction platform, where the prediction platform is configured to receive a set of non-invasive parameters corresponding to the user, receive an input corresponding to one or more selected tasks, retrieve at least one task-specific model corresponding to the one or more selected tasks based on the input, predict an outcome based on the set of non-invasive parameters and the task-specific model, where the outcome corresponds to the wellness metric, predicted values of one or more invasive parameters, or both the wellness metric and the predicted values of the one or more invasive parameters, and where the wellness metric is representative of a quantified biological parameter corresponding to the user, and provide the outcome to facilitate analysis.

DRAWINGS

These and other features and aspects of embodiments of the present specification will become better understood when the following detailed description in read with reference to the accompanying drawings in which like characters represent like parts throughout the drawings, wherein.

Figure 1:
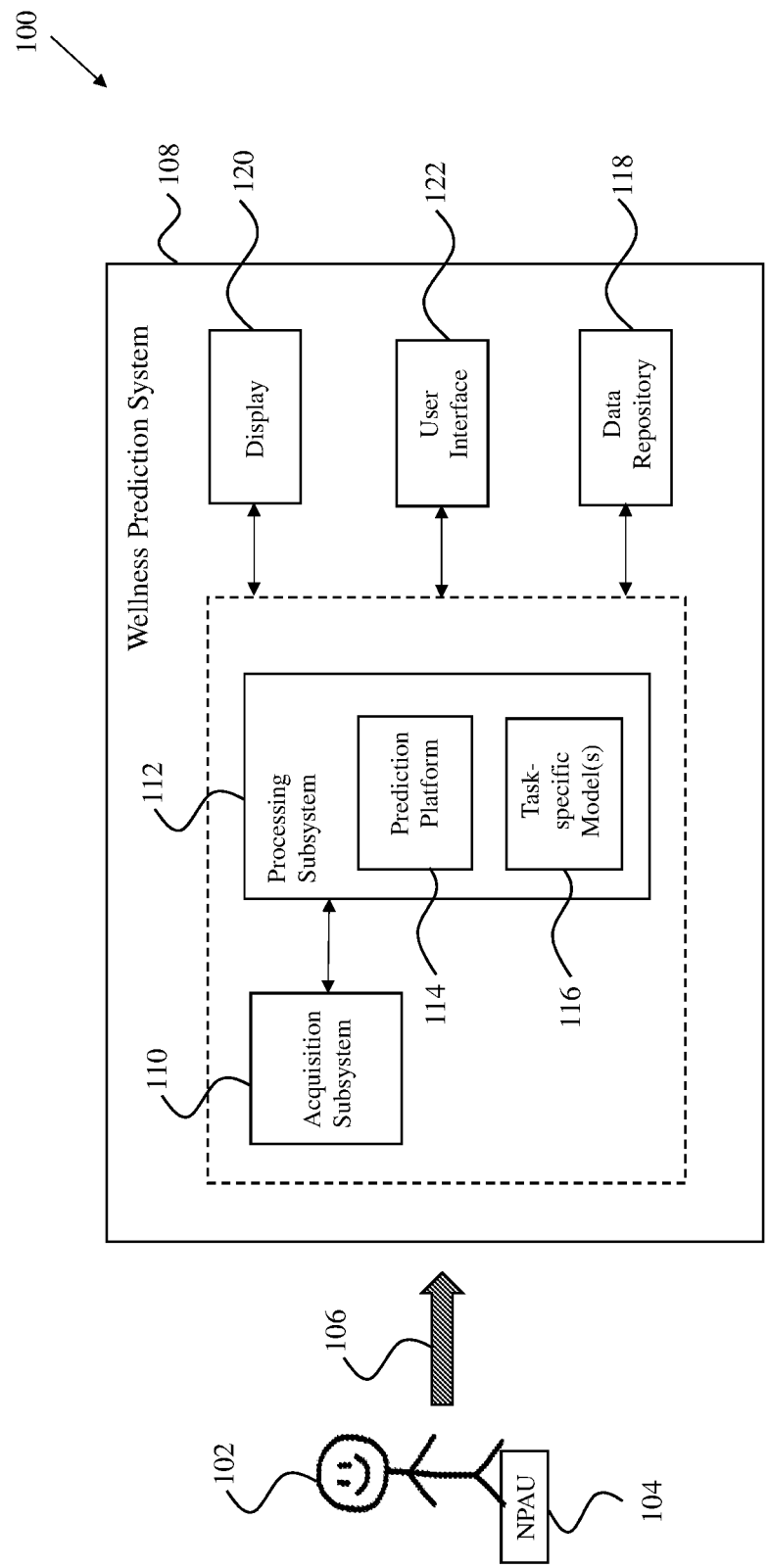
FIG. 1 is a schematic representation of an exemplary system for predicting a wellness metric, in accordance with aspects of the present specification.
Figure 3:
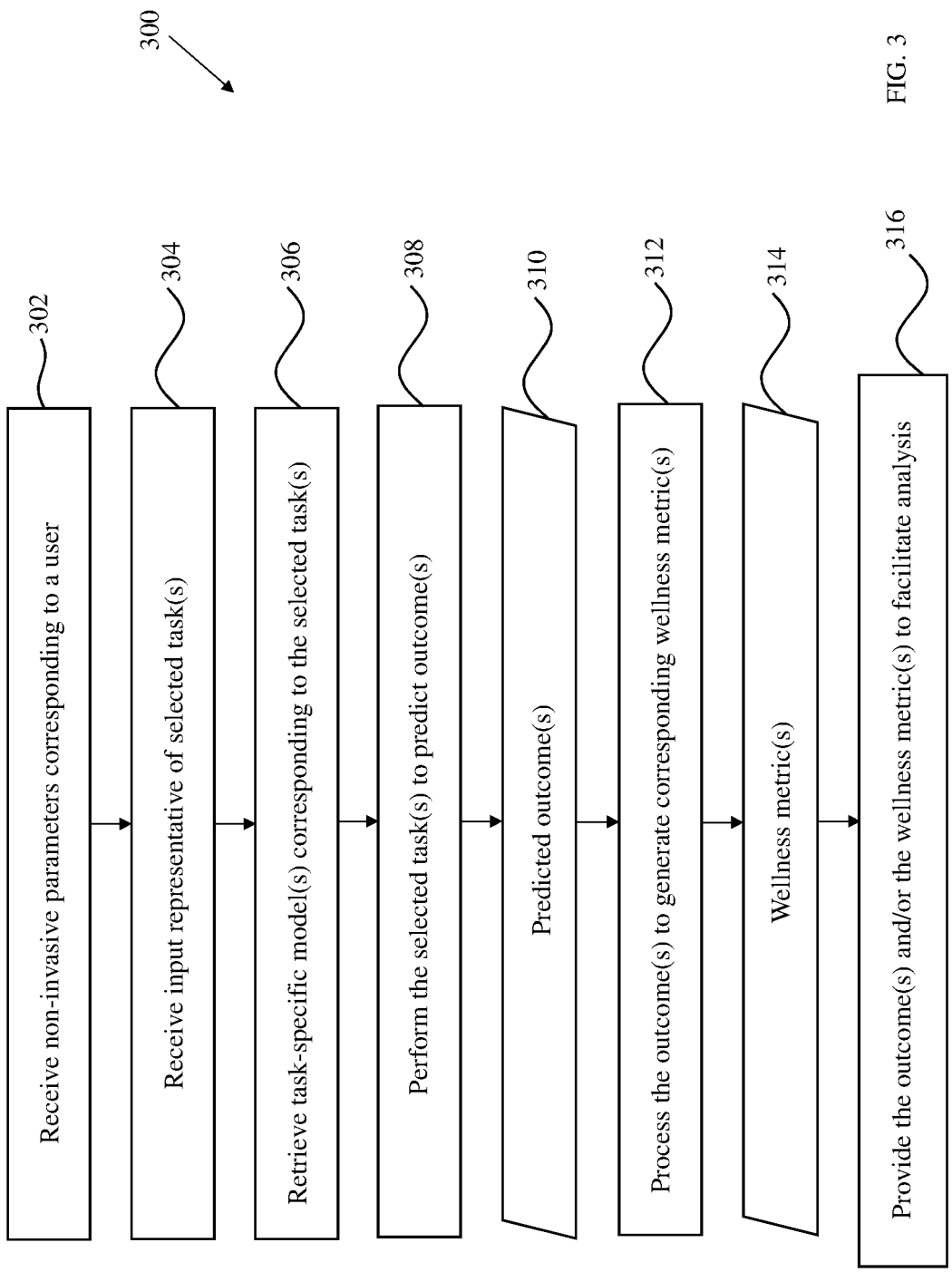
FIG. 3 is a flow chart illustrating another method for predicting a wellness metric, in accordance with aspects of the present specification.
Figure 5C:
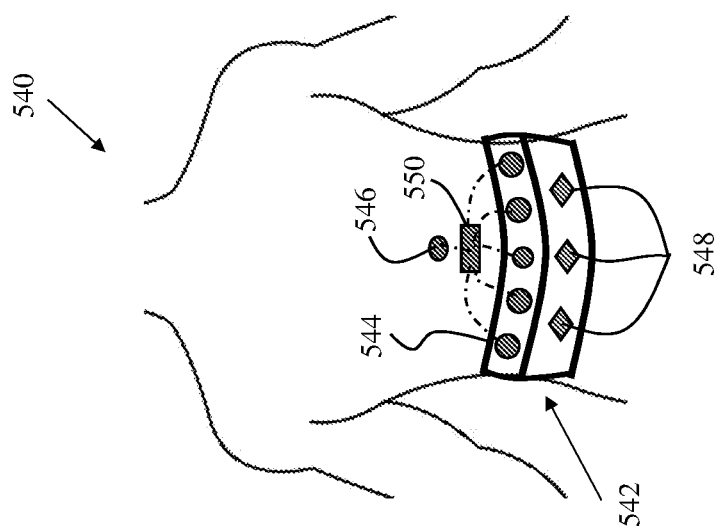
Figure 5B:
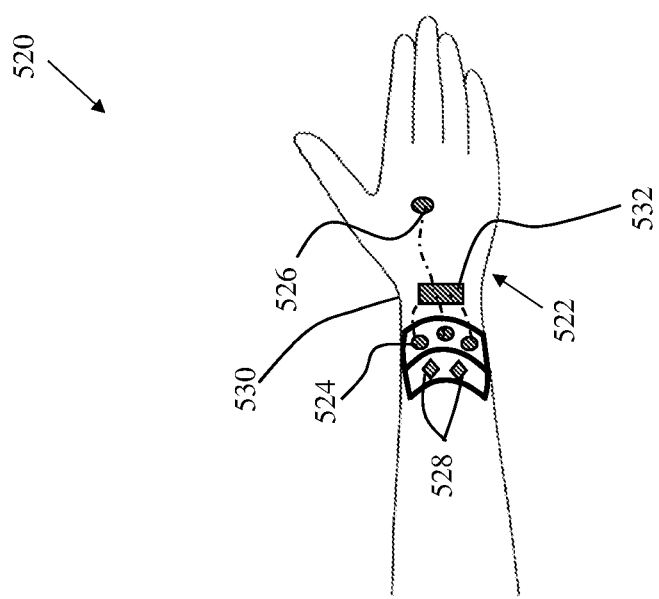
Figure 5A:
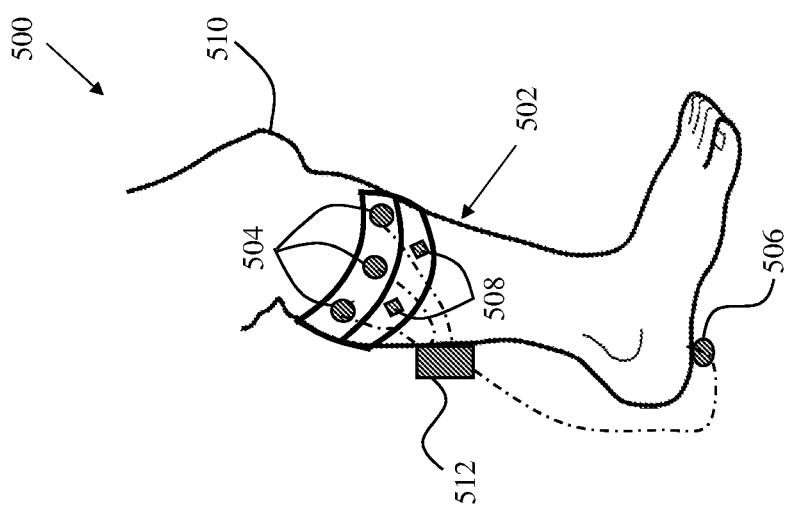
Figure 6:
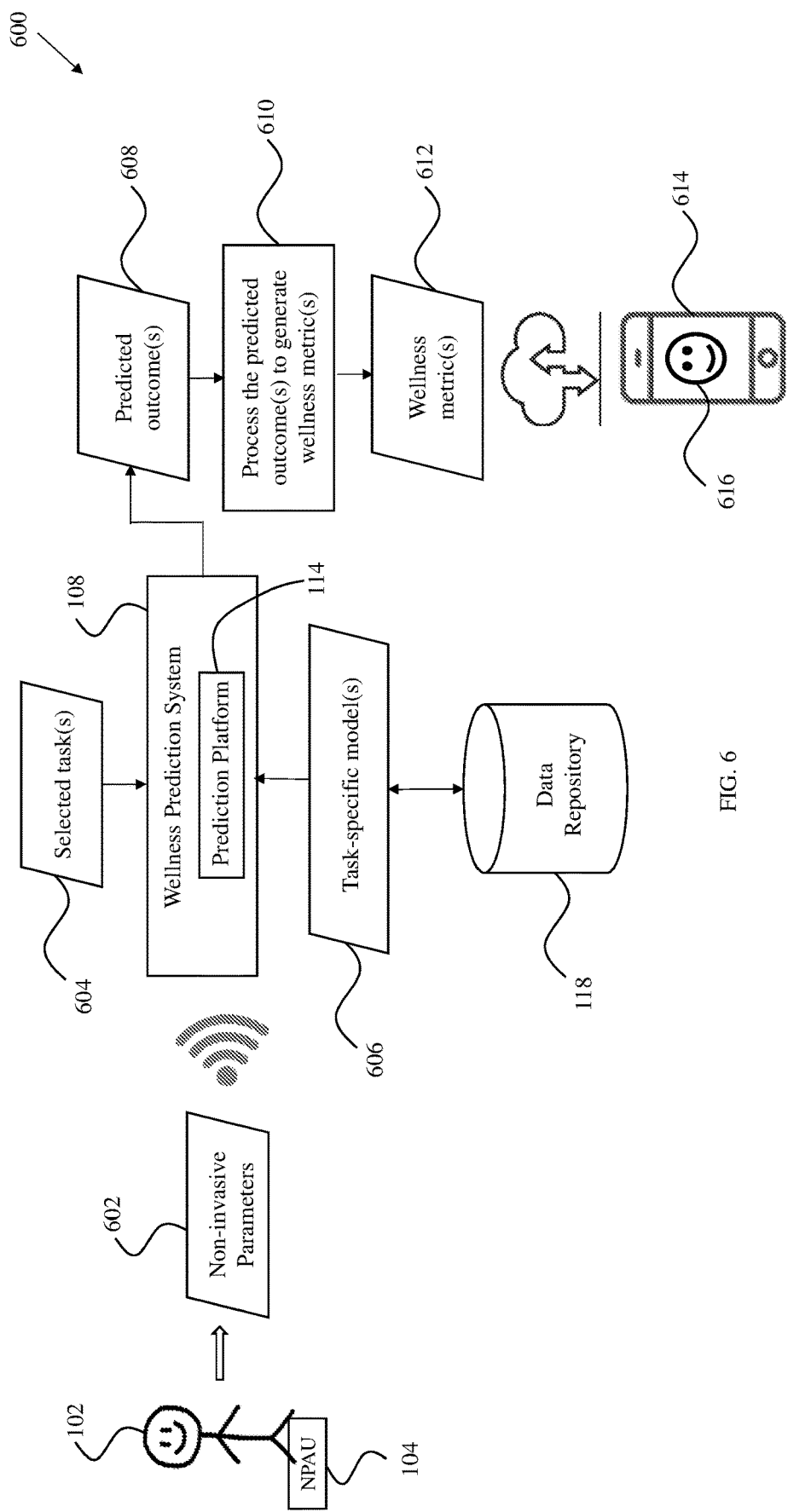
Figure 7C:
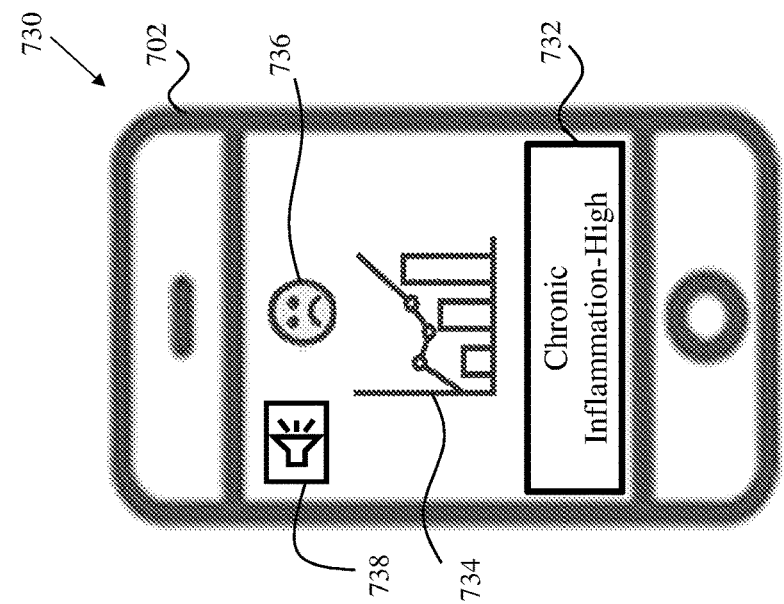
Figure 7B:
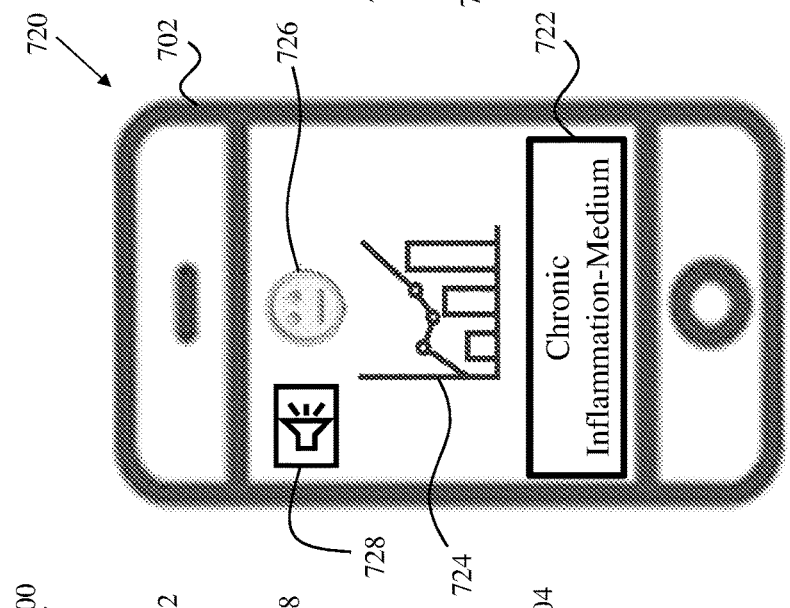
Figure 7A:
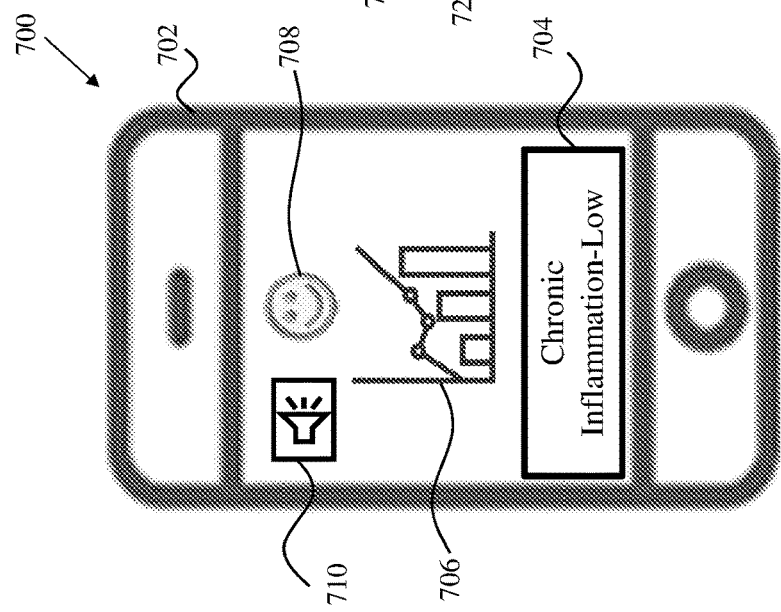
Figure 8:
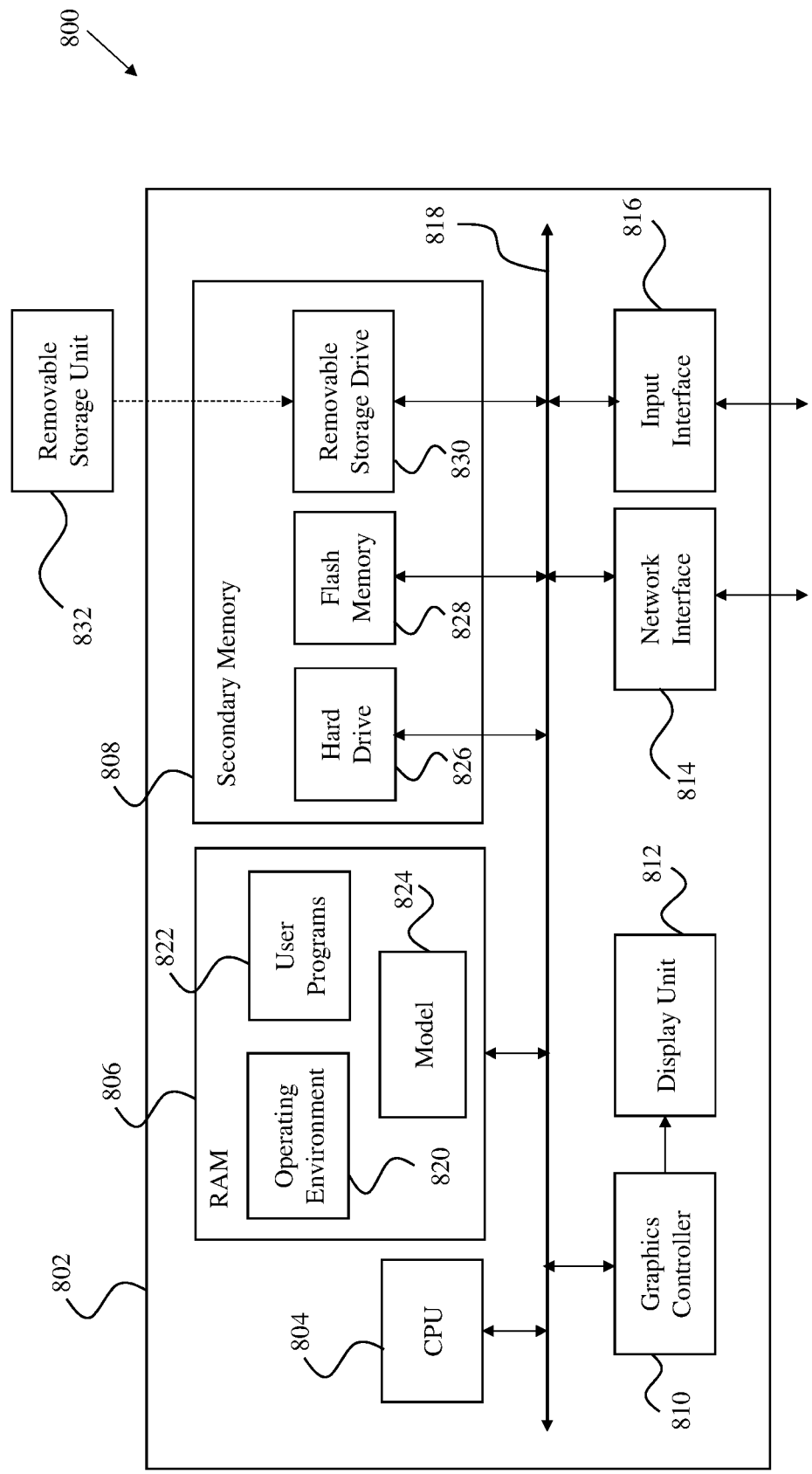

FIGS. 5(a)-5(c) are diagrammatical illustrations of different embodiments of a non-invasive parameter acquisition unit for use in the system of FIG. 1, in accordance with aspects of the present specification;

FIG. 6 is a schematic illustration of the method for predicting a wellness metric of FIG. 3, in accordance with aspects of the present specification;

FIGS. 7(a)-7(c) are diagrammatical illustrations of providing the wellness metric to facilitate analysis and/or lifestyle recommendations, in accordance with aspects of the present specification; and FIG. 8 is a schematic representation of one embodiment of a digital processing system implementing a prediction platform for use in the system of FIG. 1, in accordance with aspects of the present specification.

DETAILED DESCRIPTION

The following description presents exemplary systems and methods for predicting one or more wellness metrics using only non-invasive parameters corresponding to an object of interest such as a user. Particularly, embodiments described hereinafter present exemplary systems and methods that facilitate enhanced prediction of the wellness metrics based only on non-invasive parameters, while circumventing the need for invasive tests and/or analysis in a laboratory. Use of the present systems and methods presents significant advantages in reliably predicting quantitative measurements and/or other outcomes, thereby overcoming the drawbacks of currently available traditional methods of determining wellness metrics.

For ease of understanding, the exemplary embodiments of the present systems and methods are described in the context of a wellness prediction system configured to provide/predict wellness metrics of a user. However, use of the exemplary embodiments illustrated hereinafter in other systems and applications such as veterinary applications is also contemplated. An exemplary environment that is suitable for practising various implementations of the present systems and methods is discussed in the following sections with reference to FIG. 1.

Referring now to the drawings, FIG. 1 illustrates an exemplary system 100 for predicting one or more wellness metrics corresponding to a user 102. In particular, the system 100 is configured to predict one or more outcomes based only on a set of non-invasive parameters corresponding to the user 102. The predicted outcomes may correspond to one or more wellness metrics, a predicted value of one or more invasive parameters, or both the wellness metrics and the predicted values of one or more non-invasive parameters. In some embodiments, the predicted outcomes such as the predicted values of one or more invasive parameters may be processed to generate or predict one or more wellness metrics, where the wellness metrics may be used for lifestyle recommendations, further analysis, follow-up, and/or treatment planning. In other embodiments, the system 100 may be configured to directly provide the wellness metrics.

As used herein, the term "user" refers to a person using the system 100 for wellness management and/or disease management. Also, as used herein, the term "invasive parameter" refers to a parameter that is determined using an invasively drawn sample such as, but not limited to, a blood sample, a tissue sample, and the like. Further, as used herein, the term "invasive parameter" also encompasses in vitro parameters determined in a laboratory using other samples such as, but not limited to, a salivary sample, a urine sample, and the like. Some non-limiting examples of the invasive parameter include a C-reactive protein (CRP) value, a salivary cortisol value, a serum protein electrophoresis (SPEP or SPE) value, and the like. In a similar fashion, as used herein, the term "non-invasive parameter" refers to a parameter that is measured or determined without use of an invasively drawn sample or laboratory analysis. Consequently, the non-invasive parameter, as defined herein, may be measured and/or determined continuously. Some non-limiting examples of the non-invasive parameter include an age, a gender, height, weight, bioimpedance values, a pulse rate, heart rate variability, sweat, skin temperature, an image of the tongue, an image of the face, an image of the nails, an image of the eyes, and the like. Moreover, as used herein, the term "outcome" refers to a predicted value of one or more of the invasive parameters and/or one or more wellness metrics.

Further, as used herein, the term "wellness metric" is used to refer to a quantified biological parameter that is scientifically established to be an indicator of an individual's health and/or lifestyle. In one example, the wellness metric is a measure of at least one of the CRP, SPE, and salivary cortisol in the body of the user. By way of a non-limiting example, the wellness metrics may include an indicator of acute inflammation, chronic inflammation, stress, and the like. Additionally, the term "task" is used to refer to determining a predicted value corresponding to one or more invasive parameters and/or generating one or more wellness metrics.

During a clinical exam, the user 102 may be appropriately positioned. For example, the user 102 may be suitably seated or may be positioned on a supporting structure such as a table. Subsequently, a set of non-invasive parameters 106 may be obtained from the user 102. In a presently contemplated configuration, the system 100 includes a non-invasive parameter acquisition unit (NPAU) 104 configured to facilitate acquisition of the non-invasive parameters 106 corresponding to the user 102. The set of non-invasive parameters 106 may include one or more biological parameters corresponding to the user 102. As noted hereinabove, the non-invasive parameters 106 corresponding to the user include, but are not limited to, an age, a gender, height, weight, bioimpedance values, a pulse rate, heart rate variability, sweat, skin temperature, skin characterization, tongue characterization, face characterization, nail characterization, eye characterization, menstrual cycle, and the like.

The non-invasive parameter acquisition unit 104, in one embodiment, has a wearable form factor and may be disposed on or about the user 102. Also, the non-invasive parameter acquisition unit 104 includes one or more sensors configured to aid in acquiring the non-invasive parameters 106. Some non-limiting examples of the non-invasive parameter acquisition unit 104 include a wearable sock, a wearable glove, a wearable belt, and the like. In accordance with aspects of the present specification, use of the non-invasive parameter acquisition unit 104 having the wearable form factor aids in the continuous acquisition of the non-invasive parameters 106.

Furthermore, by way of example, some non-invasive parameters 106 such as the pulse rate, the heart rate variability, the sweat output, the skin temperature, and the like may be obtained via use of sensors (not shown) in the non-invasive parameter acquisition unit 104 or via use of other means of acquiring the non-invasive parameters 106. Moreover, some other non-invasive parameters 106 such as the age, gender, height, weight, and the menstrual cycle data may be manually provided by a clinician or may be automatically obtained. In addition, other non-invasive parameters 106 such as the face characterization, the tongue characterization, the eye characterization, and the nail characterization may be obtained via images that respectively correspond to the face, tongue, eyes, and nails of the user 102. In one non-limiting example, an imaging modality such as an ultrasound imaging system and the like may be used to obtain the images. Various embodiments of the non-invasive parameter acquisition unit 104 will be described in greater detail with reference to FIGS. 5(a)-5(c).

As depicted in FIG. 1, the system 100 includes a wellness prediction system 108. In accordance with aspects of the present specification, subsequent to the acquisition of the desired set of non-invasive parameters 106 from the user 102, the non-invasive parameters 106 are communicated to the exemplary wellness prediction system 108. In one example, the non-invasive parameters 106 may be transmitted or communicated to the wellness prediction system 108 via wired means such as a cable. In other examples, the non-invasive parameters 106 may be wirelessly transmitted to the wellness prediction system 108 via use of a network. In yet another example, the non-invasive parameters 106 may be transmitted to a remote location and/or the cloud for storage and the wellness prediction system 108 may be configured to retrieve the non-invasive parameters 106 from the remote storage location and/or cloud. Also, in certain embodiments, the non-invasive parameters 106 may be communicated to the wellness prediction system 108 in real-time. In other embodiments, the non-invasive parameters 106 may be stored and communicated to the wellness prediction system 108 at a later time.

Further, in a presently contemplated configuration, the wellness prediction system 108 may include an acquisition subsystem 110 and a processing subsystem 112. The acquisition subsystem 110 is configured to acquire the non-invasive parameters 106 corresponding to the user 102. It may be noted that in one embodiment, the acquisition subsystem 110 may be configured to directly obtain the non-invasive parameters 106 from the non-invasive parameter acquisition unit 104. However, in certain other embodiments, the acquisition subsystem 110 may obtain the non-invasive parameters 106 from a storage such as a data repository 118, an optical data storage article such as a compact disc (CD), a digital versatile disc (DVD), a Blu-ray disc, and the like.

Moreover, the non-invasive parameters 106 corresponding to the user 102 may be processed by the processing subsystem 112. In a non-limiting example, the processing subsystem 112 may include one or more application-specific processors, digital signal processors, microcomputers, graphical processing units, microcontrollers, Application Specific Integrated Circuits (ASICs), Programmable Logic Arrays (PLAs), Field Programmable Gate Arrays (FGPAs), and/or any other suitable processing devices. In alternative embodiments, the processing subsystem 112 may be configured to retrieve the non-invasive parameters 106 from the data repository 118. The data repository 118 may include a hard disk drive, a floppy disk drive, a read/write CD, a DVD, a Blu-ray disc, a flash drive, a solid-state storage device, a local database, and the like.

In addition, the examples, demonstrations, and/or process steps performed by certain components of the system 100 such as the processing subsystem 112 may be implemented by suitable code on a processor-based system, where the processor-based system may include a general-purpose computer or a special-purpose computer. Also, different implementations of the present specification may perform some or all of the steps described herein in different orders or substantially concurrently.

Currently available techniques for determining the invasive parameters entail invasive procedures to draw a sample from a user. Also, a salivary sample, a urine sample, and the like may be obtained from the user. These samples are then processed and/or analyzed in a laboratory to determine the invasive parameters. However, in accordance with aspects of the present specification, the non-invasive parameters 106 are acquired and processed by the wellness prediction system 108 to predict one or more desired outcomes such as predicted values of the invasive parameters and/or one or more wellness metrics based on the set of non-invasive parameters 106, thereby circumventing the need for invasive procedures and/or laboratory analysis. As noted hereinabove, the desired/predicted outcomes are representative of predicted values of the invasive parameters and/or wellness metrics. Moreover, in the example where the predicted outcomes include predicted values of the invasive parameters, the predicted values of the invasive parameters may be further processed by the processing subsystem 112 to generate one or more wellness metrics. Additionally or alternatively, the processing subsystem 112 may be configured to directly generate the wellness metrics from the non-invasive parameters 106.

As depicted in FIG. 1, in a presently contemplated configuration, the processing subsystem 112 includes a prediction platform 114 and one or more task-specific models 116. In certain embodiments, the task-specific models 116 may include a neural network that is trained and configured to perform one or more desired tasks. By way of example, one embodiment of the task-specific model 116 may be trained to determine a predicted value of the CRP. It may be noted that the terms neural network and neural network model may be used interchangeably.

As will be appreciated, a neural network (NN) is a computational model. Further, the neural network model includes several layers. Each layer in the neural network model in turn includes several computational nodes. The computational node is configured to perform mathematical operations based on received input to generate an output. Some non-limiting examples of the mathematical operations include summation, passing through a non-linearity, comparing a present state of the node with a previous state, and the like. Moreover, the neural network model also includes weights that are typically associated between each node in a layer and one or more nodes in subsequent layers.

The task-specific models 116 may be generated by training a model/neural network using a dataset that includes a plurality of sets of non-invasive parameters corresponding to a plurality of users, a plurality of sets of invasive parameters corresponding to the same plurality of users, and one or more tasks to be performed. As previously noted, the tasks to be performed may include determining, using the non-invasive parameters 106, a predicted value of one or more of the CRP, SPE, and salivary cortisol and/or generating one or more wellness metrics. Accordingly, the task-specific model 116 may be trained to determine a predicted value of one or more invasive parameters based only on a set of non-invasive parameters 106 and/or generate one or more wellness metrics, thereby obviating the need for invasively drawing a sample from the user 102 and/or analyzing samples in a laboratory as warranted by the presently available techniques for determining the invasive parameters and/or wellness metrics. The task-specific models 116 so generated may be stored in the data repository 118, for example.

As noted hereinabove, parameters such as the CRP, SPE, and salivary cortisol (which are markers of respective systemic conditions of body of the user/subject, as is well known in the relevant arts) are traditionally determined via use of invasive tests and/or laboratory analysis, causing discomfort to the users. In accordance with aspects of the present specification, the wellness prediction system 108 is designed to circumvent the shortcomings of the presently available techniques for determining the invasive parameters and/wellness metrics. In particular, the prediction platform 114 is configured to predict values of the invasive parameters based directly on the non-invasive parameters 106. Specifically, the prediction platform 114 is configured to process the non-invasive parameters 106 via use of one or more task-specific models 116 to predict the values of the invasive parameters and/or wellness metrics, thereby obviating the need for the traditionally performed invasive sample draws and/or any other processing steps in the laboratory that result in user discomfort. Additionally, in some embodiments, the prediction platform 114 is configured to further process the predicted values of the invasive parameters to generate one or more corresponding wellness metrics. In some other embodiments, the prediction platform 114 may be configured to directly generate the wellness metrics. The predicted values of the invasive parameters and/or the wellness metrics may then be provided to a clinician or other systems to facilitate further lifestyle recommendations, analysis, treatment planning, follow-up, and the like.

The system 100 that includes the prediction platform 114 provides a robust framework that bypasses the invasive procedures for drawing samples and/or other tests/analysis of the urine, saliva, and blood in the laboratory and directly maps the non-invasive parameters 106 to quantitative clinical results that are representative of predicted values of the invasive parameters and/or wellness metrics. The prediction platform 114 works in conjunction with the task-specific models 116 to enhance the performance of the system 100.

It may be noted that although the embodiment depicted in FIG. 1 depicts the processing subsystem 112 as including the prediction platform 114, in some embodiments, the prediction platform 114 may be employed as a standalone unit that is physically separate from the processing subsystem 112 and/or the wellness prediction system 108.

Moreover, the task-specific models 116 are trained to generate specific desired outputs. In particular, the task-specific models 116, when deployed, aid the prediction platform 114 in performing a given task to provide a desired predicted value of the non-invasive parameter and/or a desired wellness metric. For example, the prediction platform 114 may be configured to use a task-specific model 116 to process the non-invasive parameters 106 to predict a value of the salivary cortisol.

With continuing reference to FIG. 1, in one embodiment, the prediction platform 114 is configured to maintain a model. As used herein, "maintain a model" may entail generating the model and hosting the model. The model may be hosted in a data repository, the cloud, and the like. Also, the model may be hosted in a local repository, a remote repository, the cloud, and the like. Moreover, in one example, the model may include one or more task-specific models 116. Furthermore, the model is configured to receive as input a set of parameters and provide as output a wellness metric. In one example, a set of non-invasive biological parameters such as the non-invasive parameters 106 corresponding to a user such as the user 102 may be received. In addition, the set of non-invasive biological parameters may be provided as the set of parameters to the model to cause the model to generate a wellness metric corresponding to the user 102. The aspect of maintaining the model will be described in greater detail with reference to FIG. 4.

As noted hereinabove, the prediction platform 114 is configured to receive one or more non-invasive parameters 106. Additionally, in accordance with further aspects of the present specification, the prediction platform 114 is also configured to receive an input that is representative of one or more selected tasks to be performed. In one embodiment, the selected task may be provided by a clinician, for example. However, in other embodiments, the selected task may be automatically selected by the system 100.

Subsequent to receipt of the non-invasive parameters 106 and the selected task(s), the prediction platform 114 is configured to retrieve a task-specific model 116 corresponding to the selected task. In one embodiment, the prediction platform 114 is configured to query the data repository 118 to identify a corresponding task-specific model 116 based on the selected task. Additionally, the prediction platform 114 may be configured to retrieve the identified task-specific model 116. By way of a non-limiting example, if the selected task entails predicting the value of CRP, then a model 116 configured to perform the prediction of the CRP value is retrieved.

Once the task-specific model 116 is identified and retrieved, the prediction platform 114 is configured to perform the selected task using the task-specific model 116. In particular, the prediction platform 114 is configured to process the non-invasive parameters 106 in conjunction with the task-specific model 116 to generate the desired outcome(s). With continuing reference to the selected task of predicting the value of the CRP, subsequent to processing of the non-invasive parameters 106 by the prediction platform 114 via use of the task-specific model 116, a predicted value of the CRP is obtained.

Moreover, if the predicted outcome includes a predicted value of an invasive parameter, the prediction platform 114 is also configured to process the predicted value of the invasive parameter to facilitate further analysis, lifestyle recommendations, and/or treatment planning. In certain embodiments, the generated outcomes in the form of the predicted values of the invasive parameters may be processed to generate one or more wellness metrics. By way of a non-limiting example, if the outcome is a predicted value of the CRP, the predicted value may be processed by the prediction platform 114 to generate a corresponding wellness metric. In one example, a value of the wellness metric may be representative of an indicator of a quality of acute inflammation, chronic inflammation, stress, and the like. These indicators may be represented in the form of a graphic, a chart, or any other form of audio, and/or visual representation. The outcomes and/or the indicators of the wellness metrics may be visualized on an interface unit such as a display.

In certain embodiments, the task-specific models 116 may be generated by the prediction platform 114. In some embodiments, the task-specific models 116 may be generated offline. Also, these task-specific models 116 may be stored in the data repository 118, for example. In one embodiment, a plurality of sets of non-invasive parameters corresponding to a plurality of users may be obtained and provided as an input to a neural network in the prediction platform 114. Moreover, input corresponding to one or more selected tasks to be performed may be obtained. These selected tasks may also be provided as an input to the neural network in the prediction platform 114. Further, a plurality of sets of invasive parameters and/or wellness metrics corresponding to the plurality of users may also be obtained and provided to the neural network in the prediction platform 114 as a desired output. The neural network may be trained with appropriate inputs to perform a selected task, such as providing a desired output in the form of a predicted outcome such as predicted values of the invasive parameters and/or wellness metrics. Consequent to the training phase, one or more task-specific models 116 are generated. Each task-specific model 116 may be configured to perform one or more selected tasks. The method of generating the task-specific models 116 is described in greater detail with reference to FIG. 4.

As described hereinabove, in some embodiments, the prediction platform 114 is described as being configured to predict outcomes such as values of the invasive parameters based on the non-invasive parameters 106 and subsequently processing the predicted outcomes to generate one or more wellness metrics. However, in some embodiments, the prediction platform 114 may be configured to directly generate the wellness metrics based on the non-invasive parameters 106. Accordingly, in this example, task-specific models 116 trained to generate the wellness metrics may be employed.

With continuing reference to FIG. 1, the wellness prediction system 108 may include a display 120 and a user interface 122. The display 120 and the user interface 122 may overlap in some embodiments such as a touch screen. Further, in some embodiments, the display 120 and the user interface 122 may include a common area. The display 120 may be configured to visualize or present the predicted outcomes such as the predicted values of the invasive parameters. In addition, the indicators of the wellness metrics may also be displayed on the display 120.

The user interface 122 of the wellness prediction system 108 may include a human interface device (not shown) that is configured to aid a clinician in providing inputs or manipulating the outcomes and/or indicators visualized on the display 120. In certain embodiments, the human interface device may include a trackball, a joystick, a stylus, a mouse, or a touch screen. It may be noted that the user interface 122 may be configured to aid the user 102 and/or clinician in navigating through the inputs and/or outcomes/indicators generated by the wellness prediction system 108.

Implementing the wellness prediction system 108 that includes the prediction platform 114 as described hereinabove aids in enhancing the performance of the system 100 by predicting outcomes and/or generating clinically relevant wellness metrics based on non-invasive parameters 106, while obviating the need for invasive tests and/or laboratory analysis. Additionally, once the predicted outcomes such as the invasive parameters and/or clinically relevant wellness metrics are generated, the system 100 may also be configured to appropriately facilitate partnering the user 102 with fitness centers, clinical centers, hospitals, nutraceuticals, and the like, to enhance the wellness of that user 102. The working of the system 100 may be better understood with reference to FIGS. 2-6 and 7(a)-7(c).

Figure 2:
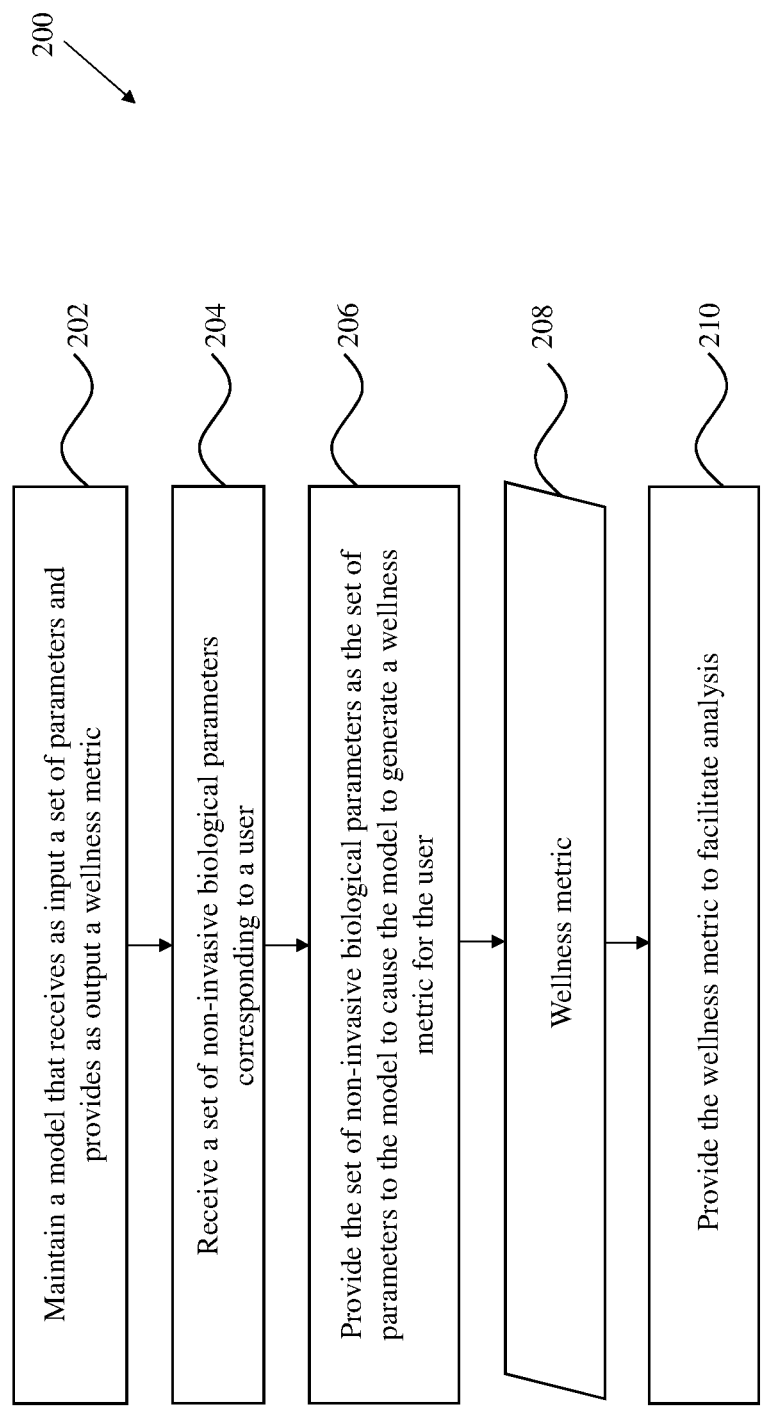
FIG. 2 is a flow chart illustrating a method for predicting a wellness metric, in accordance with aspects of the present specification.

Embodiments of the exemplary methods of FIGS. 2-3 and 6 may be described in a general context of computer executable instructions on computing systems or a processor. Generally, computer executable instructions may include routines, programs, objects, components, data structures, procedures, modules, functions, and the like that perform particular functions or implement particular abstract data types.

Moreover, the embodiments of the exemplary methods may be practised in a distributed computing environment where optimization functions are performed by remote processing devices that are linked through a wired and/or wireless communication network. In the distributed computing environment, the computer executable instructions may be located in both local and remote computer storage media, including memory storage devices.

In addition, in FIGS. 2, 3, and 6, the exemplary methods are illustrated as a collection of blocks in a logical flow chart, which represents operations that may be implemented in hardware, software, firmware, or combinations thereof. It may be noted that the various operations are depicted in the blocks to illustrate the functions that are performed. In the context of software, the blocks represent computer instructions that, when executed by one or more processing subsystems, perform the recited operations.

Moreover, the order in which the exemplary methods are described is not intended to be construed as a limitation, and any number of the described blocks may be combined in any order to implement the exemplary methods disclosed herein, or equivalent alternative methods. Further, certain blocks may be deleted from the exemplary methods or augmented by additional blocks with added functionality without departing from the spirit and scope of the subject matter described herein.

Conventional presently available techniques for determining the invasive parameters corresponding to a user call for invasively drawing a biological sample from the user and/or processing a biological sample in a laboratory to determine the invasive parameters, thereby leading to user discomfort and/or errors due to the clinician/laboratory equipment. In accordance with aspects of the present specification, the shortcomings of the presently available techniques are circumvented by directly mapping the non-invasive parameters to generate desired outcomes such as the predicted values of the invasive parameters and/or the wellness metrics. In particular, the prediction platform 114 in conjunction with the task-specific model 116 is configured to predict the invasive parameters and/or the wellness metrics using only the non-invasive parameters.

Referring to FIG. 2, a flow chart 200 of an exemplary method for predicting a wellness metric, in accordance with aspects of the present specification, is presented. In particular, the method 200 entails predicting/generating a wellness metric corresponding to a user. The method 200 of FIG. 2 is described with reference to the components of FIG. 1. Moreover, in certain embodiments, the method 200 may be performed by the prediction platform 114.

As depicted in FIG. 2, at step 202, a model is maintained. The model is configured as input a set of parameters corresponding to a user such as the user 102. Further, the model is configured to provide as output a wellness metric corresponding to the user 102. As previously noted, in certain embodiments, the prediction platform 114 is configured to maintain the model. The prediction platform 114 is configured to generate the model and host the model. The model may be employed to generate the wellness metric corresponding to the user 102 based on the input.

Further, as depicted by step 204, a set of non-invasive biological parameters such as the non-invasive parameters 106 corresponding to the user 102 is received. As previously noted, in certain embodiments, one or more of the non-invasive biological parameters 106 may be obtained via the non-invasive parameter acquisition unit 104, while some other non-invasive biological parameters 106 may be obtained as input via the user interface 122, for example. In one example, the non-invasive biological parameters 106 may be received by the prediction platform 114.

One non-limiting example of the non-invasive biological parameter 106 may include bioimpedance values that correspond to at least two frequencies. The bioimpedance values may be obtained by applying electrical signals across the tissue of the user 102. Some other examples of the non-invasive biological parameters include pulse rate, heart rate variability, skin temperature, gender, menstrual cycle data, and images of the tongue, nail and eye of the user 102.

Subsequently, at step 206, the set of non-invasive biological parameters may be provided as the set of parameters to the model. In particular, providing the set of non-invasive biological parameters to the model causes the model to generate an output. In one embodiment, the output of the model is a predicted value of a wellness metric 208 corresponding to the user 102. The wellness metric 208 may be a measure of at least one of serum protein electrophoresis (SPE), C-reactive protein (CRP), and salivary cortisol in the body of the user 102. In certain embodiments, the prediction platform 114 may be configured to process the set of non-invasive biological parameters via the model to generate the wellness metric 208.

Additionally, in some embodiments, the wellness metric 208 may be provided to facilitate further analysis, lifestyle recommendations, and/or treatment planning, as indicated by step 210. The method 200 will be described in greater detail with reference to FIGS. 4, 5(a)-5(c), 6, and 7(a)-7(c).

Turning now to FIG. 3, a flow chart 300 of another exemplary method for predicting wellness metrics using non-invasive parameters, in accordance with aspects of the present specification, is presented. In particular, the method 300 entails predicting one or more outcomes, where the outcomes include predicted values of one or more invasive parameters and/or one or more wellness metrics. The method 300 of FIG. 3 is described with reference to the components of FIGS. 1-2. Moreover, in certain embodiments, the method 300 may be performed by the prediction platform 114 in conjunction with the task-specific model(s) 116.

The method starts at step 302, where non-invasive parameters 106 corresponding to the user 102 are received. As previously noted, one or more of the non-invasive parameters 106 may be obtained via the non-invasive parameter acquisition unit 104, while some other non-invasive parameters 106 may be obtained as input via the user interface 122, for example. In accordance with aspects of the present specification, use of the non-invasive parameter acquisition unit 104 having a wearable form factor facilitates the continuous acquisition/measurement of the non-invasive parameters 106. The continuous measurement enables the capturing of the circadian rhythm and/or other long-term rhythms in the parameter being measured.

Further, input representative of one or more selected tasks may be received, as indicated by step 304. The selected tasks may be obtained automatically or as input via the user interface 122. Other means of obtaining input corresponding to the selected tasks are also contemplated. In one example, the non-invasive parameters 106 and the input corresponding to the selected tasks may be received by the prediction platform 114.

Subsequently, at step 306, one or more task-specific models 116 may be retrieved. In particular, at step 306, the task-specific model(s) 116 corresponding to the selected task(s) may be retrieved. In one example, the task-specific models 116 may be retrieved from the data repository 118. As previously noted, the task-specific models 116 may be generated offline and stored in the data repository 118. Also, the task-specific models 116 may be configured to perform a single task or a combination of tasks.

Furthermore, at step 308, the selected task(s) may be performed to predict one or more desired outcomes. More particularly, the non-invasive parameters 106 may be processed by the corresponding task-specific model 116 to continuously predict a desired outcome 310. It may be noted that at step 308 one or more predicted outcomes 310 may be generated corresponding to the selected tasks by processing the non-invasive parameters 106 by a corresponding task-specific model 116. In the example depicted in FIG. 2, the predicted outcomes 310 include predicted values of the invasive parameters.

Moreover, as depicted by step 312, the prediction platform 114 may also be configured to process the predicted outcomes 310 to continuously generate corresponding wellness metrics 314. However, in another example, step 308 may entail directly generating one or more wellness metrics 314 by processing the non-invasive parameters 106 by a task-specific model 116. In this example, control may be passed from step 308 to step 314. The continuous prediction of the wellness metrics 314 enables the capturing of the associated circadian rhythms and other long-term rhythms. Furthermore, in one example, indicators representative of the wellness metrics 314 may be generated. The indicators may be visual indicators, audio indicators, and the like.

In addition, the predicted outcomes 310 and/or the wellness metrics 314 may be provided to facilitate further analysis, lifestyle recommendations, and/or treatment planning, as indicated by step 316. The method 300 will be described in greater detail with reference to FIGS. 4, 5(a)-5(c), 6, and 7(a)-7(c).

Figure 4:
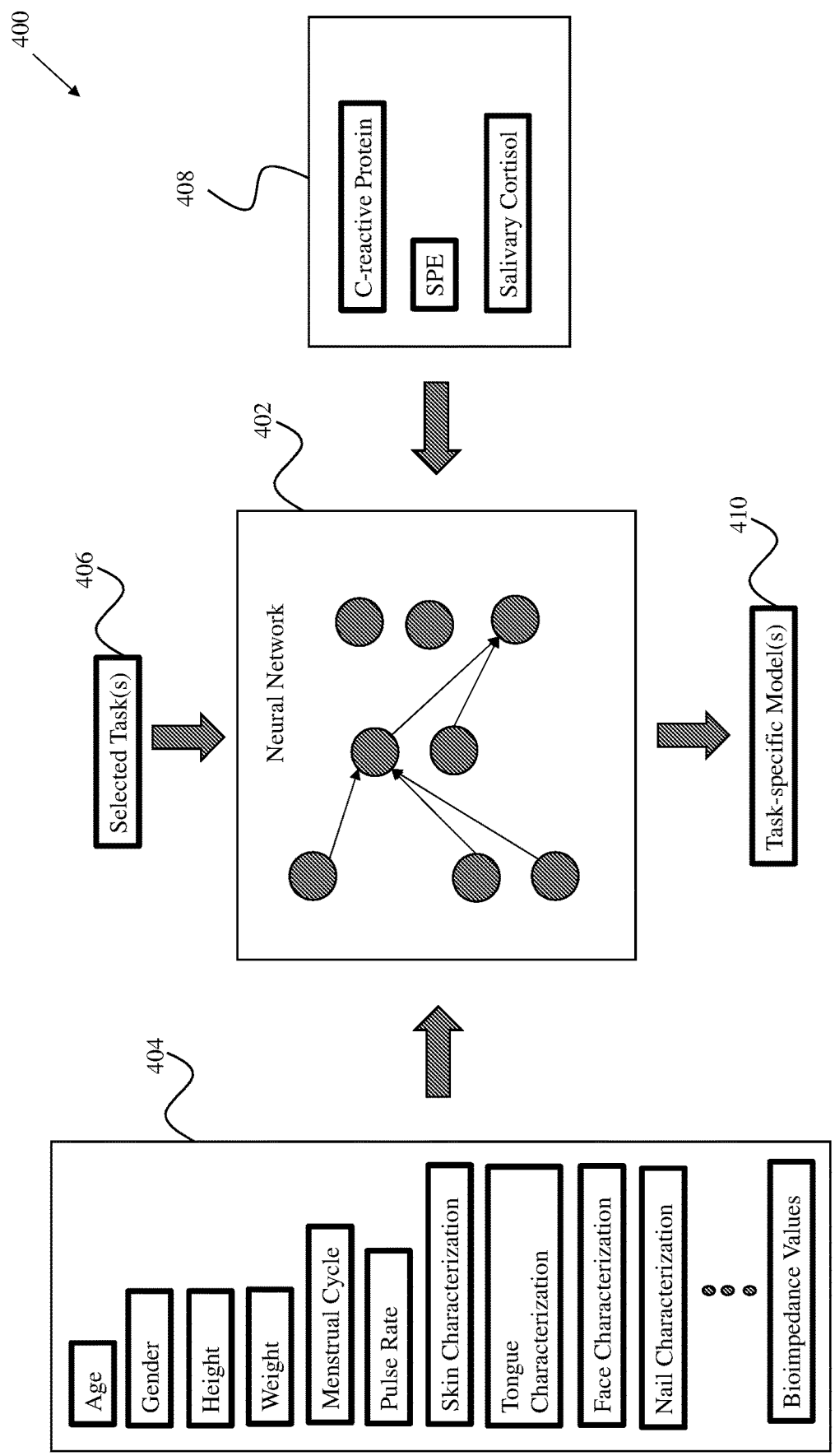
FIG. 4 is a schematic illustration of a method for generating one or more task-specific models for use in the method for predicting a wellness metric of FIGS. 2-3, in accordance with aspects of the present specification.

FIG. 4 is a schematic illustration 400 of one example of a method for generating a task-specific model such as the task-specific model 116 of FIG. 1. The method 400 of FIG. 4 is described with reference to the components of FIGS. 1-3. In one embodiment, the method 400 may be performed by the prediction platform 114.

The method 400 for generating a task-specific model entails "training" a neural network 402 to "learn" a desired task. Accordingly, the neural network 402 is trained with appropriate inputs corresponding to the desired task. In certain embodiments, the prediction platform 114 may include the neural network 402 and may be configured to generate the task-specific models.

As depicted in FIG. 4, inputs are provided to the neural network 402. In one non-limiting example, a plurality of sets of non-invasive parameters 404 corresponding to a plurality of users is acquired and provided to the neural network 402 as input. It may be noted that each set of the plurality of sets of non-invasive parameters 404 corresponds to each user of the plurality of users. Furthermore, it may also be noted that the sample set of the plurality of users is selected to be sufficient to capture diversity of age, gender, weight, height, ethnicity, and the like.

In certain embodiments, each set of non-invasive parameters 404 may include two-dimensional (2D) data such as images, time-series data such as ultrasound signals and optical signals, and bioimpedance values measured across tissue at different locations on the user's body and at different frequencies. By way of a non-limiting example, the 2D data may include images of the user's face, images of the user's tongue, images of the user's nail(s), images of the user's skin, images of the user's eyes, and the like. Some additional examples of the non-invasive parameters include an age, gender, height, weight, pulse rate, heart rate variability, menstrual cycle, and other such non-invasive parameters corresponding to the user. In addition, one or more desired/selected tasks 406 may be provided to the neural network 402.

Moreover, one or more desired outputs 408 are also provided to the neural network 402. The desired outputs 408 may include a plurality of sets of predicted values of invasive parameters and/or wellness metrics 408 corresponding to the plurality of users. Accordingly, the sets of invasive parameters 408 corresponding to the plurality of users may be acquired and provided to the neural network 402. In one example, the invasive parameters 408 may include CRP values, SPE values, salivary cortisol values, and the like. Additionally, in some examples, values representative of wellness metrics 408 such as an inflammation state in a corresponding user may also be acquired and provided to the neural network 402. As will be appreciated, the inflammation state is generally indicative of a disease state or illness in the user.

Furthermore, in certain embodiments, the invasive parameters and/or wellness metrics 408 may be acquired via clinical trials/tests performed on the plurality of users. It may be noted that each set of the plurality of sets of invasive parameters and/or wellness metrics 408 corresponds to a respective user of the plurality of users. Although the method 400 entails use of a plurality of sets of non-invasive parameters 402 and a plurality of sets of invasive parameters and/or wellness metrics 408, for ease of illustration only one set of non-invasive parameters 404 and one set of invasive parameters and/or wellness metrics 408 are depicted in FIG. 4.

Once the inputs such as the sets of non-invasive parameters 404 and the selected task(s) 406, and the desired outputs 408 such as the sets of invasive parameters and/or wellness metrics are provided to the neural network 402, the neural network 402 may be trained to perform a selected task. In particular, the neural network 402 may be trained to provide an output in the form of a predicted clinical outcome such as a wellness metric and/or a predicted value of an invasive parameter. By way of example, the neural network 402 may be trained to predict one or more of a CRP value, an SPE value, and a salivary cortisol value. Additionally or alternatively, the neural network 402 may be trained to predict one or more wellness metrics.

It may be noted that during the training or learning phase of the neural network 402, one or more model parameters in the form of weights of the neural network 402 for predicting desired outcomes may be optimized. In particular, the model parameters may be optimized such that loss between the predicted outcomes and the desired outputs 408 is minimized to ensure that the predicted outcomes closely match with the values of desired outputs 408 such as the invasive parameters and/or the wellness metrics.

Consequent to the training phase, a task-specific model 410 is generated. The task-specific model 410 may be configured to perform one or more selected tasks 406. By way of example, if the selected task 406 is prediction of a salivary cortisol value, then the task-specific model 410 is configured to facilitate prediction of a salivary cortisol value directly based on the set of non-invasive parameters 404 corresponding to a given user. It may be noted that the task-specific model 410 may be configured to perform a single task or a plurality of tasks. Also, the task-specific models 410 may be generated offline. Moreover, in one example, these task-specific models 410 may be stored in the data repository 118. In other embodiments, the task-specific models 410 may be transmitted for storage in a remote facility.

As noted hereinabove, one or more non-invasive parameters such as the non-invasive parameters 106 (see FIG. 1) may be provided to the prediction platform 114 to facilitate prediction of invasive parameters and/or wellness metrics. Moreover, as previously noted, some non-limiting examples of the non-invasive parameters 106 include biological parameters corresponding to the user 102 such as an age, a gender, height, weight, bioimpedance values, a pulse rate, heart rate variability, sweat, skin temperature, skin characterization, tongue characterization, face characterization, nail characterization, eye characterization, menstrual cycle, and the like. In some embodiments, one or more sensors are employed to obtain one or more of these non-invasive parameters 106.

Moreover, as will be appreciated, bioimpedance is representative of a response of a living organism to an externally applied electric current. In some examples, the bioimpedance is defined as a measure of opposition to the flow of the applied electric current through the tissues. Further, bioimpedance measurements have been used as a non-invasive method for measuring blood flow and body composition like total body water (TBW) and fat content. Also, the bioimpedance measurements are used in healthcare facilities to aid in disease prognosis and/or monitoring of vital body statistics. However, currently available bioimpedance measurement devices do not have a wearable form factor. Consequently, the currently available bioimpedance measurement devices do not facilitate continuous measurement without inconveniencing the user.

In accordance with exemplary aspects of the present specification, a device configured to circumvent the shortcomings of the currently available bioimpedance measurement systems/devices is presented. More particularly, the exemplary device has a wearable form factor and is configured to facilitate acquisition of a plurality of non-invasive parameters from a user, thereby facilitating continuous measurement of the various non-invasive parameters such as bioimpedance values and the like corresponding to the user.

FIGS. 5(a)-5(c) are schematic representations of exemplary non-invasive parameter measurement devices having a wearable form factor, in accordance with aspects of the present specification. In particular, various embodiments of the non-invasive parameter acquisition unit 104 are presented in FIGS. 5(a)-5(c). It may be noted that the embodiments of the non-invasive parameter acquisition unit 104 depicted in FIGS. 5(a)-5(c) are described with reference to the acquisition of bioimpedance values corresponding to the user 102. However, the non-invasive parameter acquisition unit 104 may also be configured to acquire the other non-invasive parameters. The various embodiments of the non-invasive parameter acquisition unit 104 presented in FIGS. 5(a)-5(c) are described with reference to the components of FIGS. 1-4.

It may be noted that bioimpedance values are measured corresponding to at least two frequencies to enable the task-specific models 116 to predict the wellness metrics, such as chronic inflammation. Moreover, the bioimpedance values are obtained by applying electrical signals across the tissue of the user 102.

In FIG. 5(a), a diagrammatic illustration 500 of one embodiment of a wearable non-invasive parameter acquisition unit is presented. In particular, the wearable non-invasive parameter acquisition unit 500 is in the form of a wearable sock 502. The wearable sock 502 may be worn by a user such as the user 102. Moreover, in one embodiment, a plurality of bioimpedance sensors 504, 506 and/or other sensors 508 may be arranged on or within the wearable sock 502. Further, in the example of FIG. 5(a), the bioimpedance sensors 504, 506 may be electrical contacts or contact sensors configured to measure bioimpedance. Additionally, in the embodiment depicted in FIG. 5(a), the bioimpedance electrical contacts 504 are arranged along a periphery of one end of the wearable sock 502. In one non-limiting example, the bioimpedance electrical contacts 504 may be positioned on or about the wearable sock 502 such that the bioimpedance electrical contacts 504 are disposed around at least a portion of the upper part of the user's leg and close to the knee 510 when the wearable sock 502 is disposed on the user's leg. It may be noted that each bioimpedance electrical contact 504 is operatively coupled to at least one other bioimpedance electrical contact 504 in the plurality of bioimpedance electrical contacts 504. Additionally, in one example, another bioimpedance sensor such as the bioimpedance electrical contact 506 may be positioned about the sole of the user's foot when the wearable sock 502 is worn by the user 102. This arrangement of the bioimpedance electrical contacts 504, 506 provides a plurality of bioimpedance measurement values as opposed to a single measurement provided by the currently available bioimpedance measuring devices. Other sensors 508 such as temperature sensors, pressure sensors, pulse rate sensors, and the like may be similarly arranged on or about the wearable sock 502 to facilitate acquisition of corresponding non-invasive parameters.

Moreover, each of the bioimpedance electrical contacts 504, 506 may also be operatively coupled to a junction unit 512. The junction unit 512 may be a multiplexer unit, in certain embodiments. In one example, the junction unit 512 may be disposed on the wearable sock 502 such that the junction unit 512 is positioned about a calf muscle of the user 102 when the wearable sock 502 is disposed on the user's leg. The junction unit 512 is configured to measure bioimpedance between each bioimpedance electrical contact 504 and other bioimpedance electrical contacts 504. In addition, the junction unit 512 may also be configured to measure bioimpedance between each bioimpedance electrical contact 504 and the bioimpedance electrical contact 506.

It may be noted that the bioimpedance electrical contacts 504, 506 may be operatively coupled to each other either wirelessly or via wired means. In a similar manner, the bioimpedance electrical contacts 504, 506 may be operatively coupled to the junction unit 512 either wirelessly or via wired means.

In accordance with aspects of the present specification, the design of the wearable sock 502 having the bioimpedance electrical contacts 504, 506 and/or other sensors 508 allows the continuous measurement of bioimpedance values and other non-invasive parameters as opposed to the currently available bioimpedance measuring devices that provide a single bioimpedance measurement.

Referring now to FIG. 5(b), a schematic representation of another embodiment 520 of an exemplary wearable non-invasive parameter acquisition unit having a wearable form factor, in accordance with aspects of the present specification, is illustrated. More particularly, in a presently contemplated configuration depicted in FIG. 5(b), a wearable non-invasive parameter acquisition unit 520 in the form of a wearable glove 522 configured to be worn by the user 102 and positioned about the user's arm/hand is presented.

As depicted in FIG. 5(b), in one embodiment, a plurality of bioimpedance sensors 524, 526 and/or other sensors 528 may be arranged on or within the wearable glove 522. In one embodiment, the bioimpedance sensors 524, 526 may be electrical contacts or contact sensors configured to measure bioimpedance. In a presently contemplated configuration, the bioimpedance electrical contacts 524 are arranged along a periphery of one end of the wearable glove 522. By way of a non-limiting example, the bioimpedance electrical contacts 524 may be positioned on or about the wearable glove 522 such that the bioimpedance electrical contacts 524 are disposed around at least a portion of the upper part of the user's arm and close to the wrist 530 when the wearable glove 522 is worn by the user 102. Further, each bioimpedance electrical contact 524 is operatively coupled to at least one other bioimpedance electrical contact 524 in the plurality of bioimpedance electrical contacts 524. Also, as depicted in FIG. 5(*b*), another bioimpedance sensor such as the bioimpedance electrical contact 526 may be positioned about the palm of the user's hand when the wearable glove 522 is worn by the user 102. This arrangement of the bioimpedance electrical contacts 524, 526 provides a plurality of bioimpedance measurement values as opposed to a single bioimpedance measurement provided by the currently available bioimpedance measuring devices. Moreover, other sensors 528 such as temperature sensors, pressure sensors, pulse rate sensors, and the like may be similarly arranged on or about the wearable glove 522 to facilitate acquisition of corresponding non-invasive parameters.

With continuing reference to FIG. 5(*b*), each of the bioimpedance electrical contacts 524, 526 may also be operatively coupled to a junction unit 532. In one embodiment, the junction unit 532 may be a multiplexer unit. Further, in one example, the junction unit 532 may be disposed on the wearable glove 522 such that the junction unit 532 is positioned about the wrist 530 of the user 102 when the wearable glove 532 is disposed on the user's arm/hand. The junction unit 532 is configured to measure bioimpedance between each bioimpedance electrical contact 524 and other bioimpedance electrical contacts 524. Additionally, the junction unit 532 may also be configured to measure bioimpedance between each bioimpedance electrical contact 524 and the bioimpedance electrical contact 526.

Furthermore, the bioimpedance electrical contacts 524, 526 may be operatively coupled to each other either wirelessly or via wired means. Similarly, the bioimpedance electrical contacts 524, 526 may be operatively coupled to the junction unit 532 either wirelessly or via wired means.

In accordance with aspects of the present specification, the design of the wearable glove 522 having the bioimpedance electrical contacts 524, 526 and/or other sensors 528 allows the continuous measurement of bioimpedance values and other non-invasive parameters as opposed to the currently available bioimpedance measuring devices that provide a single bioimpedance measurement.

FIG. 5(*c*) illustrates a schematic representation of yet another embodiment 540 of an exemplary wearable non-invasive parameter acquisition unit having a wearable form factor, in accordance with aspects of the present specification. In particular, in a presently contemplated configuration depicted in FIG. 5(*c*), a wearable non-invasive parameter acquisition unit 540 in the form of a wearable belt 542 configured to be worn by the user 102 and positioned about the user's abdominal region or waist is presented.

In one embodiment, a plurality of bioimpedance sensors 544, 546 and/or other sensors 548 may be arranged on or within the wearable belt 542. The bioimpedance sensors 544, 546 may be electrical contacts or contact sensors configured to measure bioimpedance, in some embodiments. Moreover, in a presently contemplated configuration, the bioimpedance electrical contacts 544 are arranged along a periphery of one end of the wearable belt 542. By way of a non-limiting example, the bioimpedance electrical contacts 544 may be positioned on or about the wearable belt 542 such that the bioimpedance electrical contacts 544 are disposed around at least a portion of the waist or abdominal region of the user 102 when the wearable belt 542 is worn by the user 102. Also, each bioimpedance electrical contact 544 is operatively coupled to at least one other bioimpedance electrical contact 544 in the plurality of bioimpedance electrical contacts 544. Further, as depicted in FIG. 5(*c*), another bioimpedance sensor such as the bioimpedance electrical contact 546 may be positioned about the navel of the user 102 when the wearable belt 542 is worn by the user 102. This arrangement of the bioimpedance electrical contacts 544, 546 provides a plurality of bioimpedance measurement values as opposed to a single bioimpedance measurement provided by the currently available bioimpedance measuring devices. Other sensors 528 such as temperature sensors, pressure sensors, pulse rate sensors, and the like may be similarly arranged on or about the wearable belt 542 to facilitate acquisition of corresponding non-invasive parameters.

Moreover, each of the bioimpedance electrical contacts 544, 546 may also be operatively coupled to a junction unit 550. In one embodiment, the junction unit 550 may be a multiplexer unit. Also, in one example, the junction unit 550 may be disposed on the wearable belt 542 such that the junction unit 550 is positioned about the waist of the user 102 when the wearable belt 542 is disposed on the user 102. The junction unit 550 is configured to measure bioimpedance between each bioimpedance electrical contact 544 and other bioimpedance electrical contacts 544. Further, the junction unit 550 may also be configured to measure bioimpedance between each bioimpedance electrical contact 544 and the bioimpedance electrical contact 546.

In addition, the bioimpedance electrical contacts 544, 546 may be operatively coupled to each other either wirelessly or via wired means. Similarly, the bioimpedance electrical contacts 544, 546 may be operatively coupled to the junction unit 550 either wirelessly or via wired means.

In accordance with aspects of the present specification, the design of the wearable belt 542 having the bioimpedance electrical contacts 544, 546 and/or other sensors 548 allows the continuous measurement of bioimpedance values and other non-invasive parameters as opposed to the currently available bioimpedance measuring devices that provide a single bioimpedance measurement.

It may be noted that the various embodiments of the exemplary wearable non-invasive parameter acquisition unit presented in FIGS. 5(*a*)-5(*c*) are for illustrative purposes and other embodiments such as, but not limited to, a wearable vest are also envisioned. Additionally, the number of sensors used and the locations of the various components of the exemplary wearable non-invasive parameter acquisition units are as depicted for ease of illustration. Other designs are also anticipated.

FIG. 6 is a schematic illustration 600 of the method 300 for predicting a wellness metric of FIG. 3. The method 600 is described with reference to the components of FIGS. 1-4 and 5(*a*)-5(*c*). The wellness prediction system 108 and the prediction platform 114 in particular is configured to receive as input one or more non-invasive parameters 602 and one or more selected tasks 604. As previously noted, in certain embodiments, the non-invasive parameters 602 corresponding to the user 102 may be acquired via use of the non-invasive parameter acquisition unit 104. Furthermore, based on the selected task 604, the prediction platform 114 is configured to retrieve a corresponding task-specific model 606 from the data repository 118.

Moreover, the prediction platform 114 is configured to process the non-invasive parameters 602 via use of the task-specific model 606. To that end, the prediction platform 114 and in particular the neural network 402 in the prediction platform 114 may include one or more dense layers (not shown), and/or one or more convolutional layers (not shown). Additionally, the neural network 402 in the prediction platform 114 may include one or more classification layers configured to predict a class of output. The dense layers may be configured to perform linear combinations of layer inputs and layer weights followed by non-linear operations such as, but not limited to, sigmoid or hyperbolic tangent or rectified linear unit functions. Moreover, the convolutional layers may be configured to perform series of convolution, normalization, and regularization operations on the layer inputs with kernel weights followed by the non-linear operations. Additionally, the prediction platform 114 may also include convolutional network (CNN) layers (not shown). The CNN layers may be configured to perform the selected task based on input from the previous layers. Consequent to processing of the non-invasive parameters 602 using the task-specific model 606, a desired outcome 608 is predicted. In the example of FIG. 6, if the selected task 604 includes prediction of the CRP value, accordingly, the predicted outcome 608 is a predicted CRP value that is determined based only on the non-invasive parameters 602.

Subsequently, as indicated by step 610, the predicted outcome 608 may be processed by the prediction platform 114 to generate one or more wellness metrics 612. It may be noted that in certain embodiments, the prediction platform 114 may be configured to directly generate the wellness metrics 612. In this example, step 610 may be bypassed and the wellness metrics 612 may be directly generated by processing the non-invasive parameters 602 via use of the task-specific model 606. As previously noted, the term "wellness metric" is used to refer to quantified biological parameters scientifically established to indicate the state of an individual's health. Some non-limiting examples of the wellness metrics may include an indicator of acute inflammation, chronic inflammation, stress, and the like. In certain embodiments, one or more indicators that are representative of the wellness metrics 612 may be generated by the prediction platform 114. The indicator may be an audio indicator, a video indicator, a text box that includes written text and/or a numeric value indicative of the wellness metric, and the like. In another example, the indicator may be a graphical representation of the wellness metric 612. By way of example, the graphical representation of the wellness metric 612 may depict a trend of a corresponding wellness metric 612.

In yet another example, the indicator may be an icon or an emoticon that is representative of the wellness metric 612. For example, a shape and/or color of the icon/emoticon may be used to represent a "state" or "quality" of the wellness metric 612. In particular, a green color emoticon may be representative of a "no disease state" or a "low-grade disease state," while a red color emoticon may be representative of an "acute disease state." Some other examples of the indicator include quality metrics in the form of text, numerical values, quality bars or other shapes, where the quality metrics are generally representative of a "state" or "quality" of the wellness metric 612. The quality bars may have a horizontal orientation or a vertical orientation. Also, these bars may be color quality bars, where one or more colors may be used in the quality bars to represent the "quality" or "state" of the wellness metrics 612. By way of example, a green color bar may represent a "healthy state," while a red color bar may represent an "acute disease state." In yet another embodiment, one or more of these indicators may be convolved to generate a composite indicator or quality metric.

The predicted outcomes 608 and/or the wellness metrics 612 so generated may be communicated as feedback to aid in enhancing clinical workflow. For example, the predicted outcomes 608 and/or the wellness metrics 612 may be communicated to a clinician or a device for further analysis, lifestyle recommendations, treatment planning, triaging, and/or storage. In certain embodiments, the predicted outcomes 608 and/or the wellness metrics 612 may be communicated for visualization on a display such as the display 120 or a mobile device such as a cellular phone 614. Reference numeral 616 is generally representative of an indicator of a wellness metric 612. Moreover, in some embodiments, the indicator(s) 616 may be positioned at convenient locations on the display unit 120 and/or cellular phone 614. The predicted outcomes 608 and/or the wellness metrics 612 may be communicated via the cloud, wired means, wireless means, and the like.

Turning now to FIGS. 7(*a*)-7(*c*), diagrammatical representations of some examples of performance of the system for predicting a wellness metric 100 of FIG. 1 and the methods for predicting a wellness metric 200, 300 of FIGS. 2-3 are presented. In particular, the examples of FIGS. 7(*a*)-7(*c*) are diagrammatical illustrations of providing the wellness metric to facilitate analysis and/or lifestyle recommendations, Also, FIGS. 7(*a*)-7(*c*) are described with reference to the components of FIGS. 1-4, 5(*a*)-5(*c*), and 6.

In the examples depicted in FIGS. 7(*a*)-7(*c*), schematic illustrations of a visualization of the predicted outcomes 608 and the wellness metrics 612 are presented. As previously noted, the wellness prediction system 108 and the prediction platform 114 in particular generate and communicate the predicted outcomes 608 and/or the wellness metrics 612 for visualization and/or storage to facilitate further analysis/lifestyle recommendations. It may be noted that in the example embodiments of FIGS. 7(*a*)-7(*c*), the predicted outcomes 608 and the wellness metrics 612 are visualized on a handheld device such as a cell phone. However, other means of visualization are also anticipated. Moreover, as previously noted, the wellness metrics 612 may include chronic inflammation, acute inflammation, stress, and the like. It may be noted that FIGS. 7(*a*)-7(*c*) present examples of the wellness metric "chronic inflammation."

Referring now to FIG. 7(*a*), a schematic representation 700 of one example of visualization of an output generated by the system 100 on a cell phone or handheld device 702 is depicted. In the example of FIG. 7(*a*), the wellness metric generated is a "chronic inflammation." Additionally, the "quality" or "state" of the chronic inflammation is indicated as "low." These outputs are represented in the form of a text box 704. Furthermore, predicted trends of the outcomes such as CRP, SPE, salivary cortisol, and the like are presented as a graphical representation 706. Moreover, the "chronic inflammation-low" state may also be represented in the form of an emoticon 708. In this example, the emoticon 708 may have a green color to indicate the "chronic inflammation-low" state. Also, an audio indicator 710 of the "chronic inflammation-low" state may be visualized.

FIG. 7(*b*) illustrates a schematic representation 720 of another example of visualization of an output generated by the system 100. In the example of FIG. 7(*b*), the wellness metric generated is a "chronic inflammation," however, the "quality" or "state" of the chronic inflammation is designated as "medium." The generated wellness metric is represented in the form of a text box 722. Additionally, the example of FIG. 7(*b*) also includes a graphical representation 724 of predicted trends of the outcomes such as CRP, SPE, salivary cortisol, and the like. Furthermore, the "chronic inflammation-medium" state may also be represented in the form of an emoticon 726. In this example, the emoticon 726 may have a yellow color to indicate the "chronic inflammation-medium" state. An audio indicator 728 of the "chronic inflammation-medium" state may be presented.

Similarly, FIG. 7(c) depicts a schematic representation 730 of yet another example of visualization of an output generated by the wellness prediction system 100. In the example of FIG. 7(c), the wellness metric generated is a "chronic inflammation." Moreover, the "quality" or "state" of the chronic inflammation is designated as "high." The generated wellness metric is represented in the form of a text box 732. Further, the example of FIG. 7(c) also includes a graphical representation 734 of predicted trends of the outcomes such as CRP, SPE, salivary cortisol, and the like. Also, the "chronic inflammation-high" state may also be represented in the form of an emoticon 736. In addition, the emoticon 736 may have a red color to indicate the "chronic inflammation-high" state. An audio indicator 738 of the "chronic inflammation-high" state may also be presented.

The visual representations of the predicted outcomes 608 and/or the wellness metrics 612 as depicted in FIGS. 7(a)-7(c) present a convenient snapshot of the "wellness state" of the user 102 to a clinician and/or the user 102, thereby enhancing the clinical workflow.

It may be noted that the various examples of the visual representations presented in FIGS. 7(a)-7(c) are for illustrative purposes. Other designs are also anticipated.

Referring now to FIG. 8, a schematic representation 800 of one embodiment 802 of a digital processing system is shown there. Digital processing system 802 may correspond to a cell phone (or other end user device) providing the user interfaces shown in FIGS. 7(a)-7(c) and/or prediction plant 114, even though the description is continued assuming digital processing system implements the prediction platform 114 (see FIG. 1), in accordance with aspects of the present specification. Also, FIG. 8 is described with reference to the components of FIGS. 1-4, 5(a)-5(c), 6, and 7(a)-7(c).

It may be noted that while the prediction platform 114 is shown as being a part of the wellness prediction system 108, in certain embodiments, the prediction platform 114 may also be integrated into end user systems such as, but not limited to, the phone 614 (see FIG. 6). Moreover, the example of the digital processing system 802 presented in FIG. 8 is for illustrative purposes. Other designs are also anticipated.

The digital processing system 802 may contain one or more processors such as a central processing unit (CPU) 804, a random access memory (RAM) 806, a secondary memory 808, a graphics controller 810, a display unit 812, a network interface 814, and an input interface 816. It may be noted that the components of the digital processing system 802 except the display unit 812 may communicate with each other over a communication path 818. In certain embodiments, the communication path 818 may include several buses, as is well known in the relevant arts.

The CPU 804 may execute instructions stored in the RAM 806 to provide several features of the present specification. Moreover, the CPU 804 may include multiple processing units, with each processing unit potentially being designed for a specific task. Alternatively, the CPU 804 may include only a single general-purpose processing unit.

Furthermore, the RAM 806 may receive instructions from the secondary memory 808 using the communication path 818. Also, in the embodiment of FIG. 8, the RAM 806 is shown as including software instructions constituting a shared operating environment 820 and/or other user programs 822 (such as other applications, DBMS, and the like). In addition to the shared operating environment 820, the RAM 806 may also include other software programs such as device drivers, virtual machines, and the like, which provide a (common) run time environment for execution of other/user programs. Moreover, in certain embodiments, the RAM may also include a model 824. The model 824 may be the task-specific models 116 (see FIG. 1).

With continuing reference to FIG. 8, the graphics controller 810 is configured to generate display signals (e.g., in RGB format) for display on the display unit 812 based on data/instructions received from the CPU 804. The display unit 812 may include a display screen to display images defined by the display signals. Furthermore, the input interface 816 may correspond to a keyboard and a pointing device (e.g., a touchpad, a mouse, and the like) and may be used to provide inputs. In addition, the network interface 814 may be configured to provide connectivity to a network (e.g., using Internet Protocol), and may be used to communicate with other systems connected to a network, for example.

Moreover, the secondary memory 808 may include a hard drive 826, a flash memory 828, and a removable storage drive 830. The secondary memory 808 may store data generated by the system 100 (see FIG. 1) and software instructions (for example, for implementing the various features of the present specification), which enable the digital processing system 802 to provide several features in accordance with the present specification. The code/instructions stored in the secondary memory 808 may either be copied to the RAM 806 prior to execution by the CPU 804 for higher execution speeds or may be directly executed by the CPU 804.

Some or all of the data and/or instructions may be provided on a removable storage unit 832, and the data and/or instructions may be read and provided by the removable storage drive 830 to the CPU 804. Further, the removable storage unit 832 may be implemented using medium and storage format compatible with the removable storage drive 830 such that the removable storage drive 830 can read the data and/or instructions. Thus, the removable storage unit 832 includes a computer readable (storage) medium having stored therein computer software and/or data. However, the computer (or machine, in general) readable medium can also be in other forms (e.g., non-removable, random access, and the like.).

It may be noted that as used herein, the term "computer program product" is used to generally refer to the removable storage unit 832 or a hard disk installed in the hard drive 826. These computer program products are means for providing software to the digital processing system 802. The CPU 804 may retrieve the software instructions and execute the instructions to provide various features of the present specification.

Also, the term "storage media/medium" as used herein refers to any non-transitory media that store data and/or instructions that cause a machine to operate in a specific fashion. Such storage media may include non-volatile media and/or volatile media. Non-volatile media include, for example, optical disks, magnetic disks, or solid-state drives, such as the secondary memory 808. Volatile media include dynamic memory, such as the RAM 806. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media.

For example, the transmission media may include coaxial cables, copper wire, and fiber optics, including the wires that include the communication path 818. Moreover, the transmission media can also take the form of acoustic or light waves, such as those generated during radio-wave and infra-red data communications.

Reference throughout this specification to "one embodiment," "an embodiment," or similar language means that a particular feature, structure, or characteristic described in connection with the embodiment is included in at least one embodiment of the present specification. Thus, appearances of the phrases "in one embodiment," "in an embodiment" and similar language throughout this specification may, but do not necessarily, all refer to the same embodiment.

Furthermore, the described features, structures, or characteristics of the specification may be combined in any suitable manner in one or more embodiments. In the description presented hereinabove, numerous specific details are provided such as examples of programming, software modules, user selections, network transactions, database queries, database structures, hardware modules, hardware circuits, hardware chips, and the like, to provide a thorough understanding of embodiments of the specification.

The aforementioned components may be dedicated hardware elements such as circuit boards with digital signal processors or may be software running on a general-purpose computer or processor such as a commercial, off-the-shelf personal computer (PC). The various components may be combined or separated according to various embodiments of the invention.

Furthermore, the foregoing examples, demonstrations, and process steps such as those that may be performed by the system may be implemented by suitable code on a processor-based system, such as a general-purpose or special-purpose computer. It should also be noted that different implementations of the present specification may perform some or all of the steps described herein in different orders or substantially concurrently, that is, in parallel. Furthermore, the functions may be implemented in a variety of programming languages, including but not limited to C++, Python, and Java. Such code may be stored or adapted for storage on one or more tangible, machine readable media, such as on data repository chips, local or remote hard disks, optical disks (that is, CDs or DVDs), memory or other media, which may be accessed by a processor-based system to execute the stored code. Note that the tangible media may include paper or another suitable medium upon which the instructions are printed. For instance, the instructions may be electronically captured via optical scanning of the paper or other medium, then compiled, interpreted or otherwise processed in a suitable manner if necessary, and then stored in the data repository or memory.

Embodiments of the systems and methods for predicting a wellness metric described hereinabove advantageously present a robust framework for predicting desired outcomes directly from non-invasive parameters corresponding to a user instead of invasive tests and/or laboratory analysis and probable loss of information and errors during these invasive tests/laboratory analyses. Additionally, the systems and methods presented herein generate wellness metrics either directly based on the non-invasive parameters or based on the predicted outcomes, thereby providing significant advantages in reliably predicting the quantitative measurements or outcomes where traditional methods tend to fail. Moreover, use of the systems and methods described herein allow the continuous acquisition of the non-invasive parameters and hence facilitate the continuous prediction of the outcomes such as predicted values of the invasive parameters and/or wellness metrics.

Also, intelligence inferred from the clinical data to generate the task-specific models provides a robust framework for use in predicting the outcomes and generating the wellness metrics. Additionally, by obviating the need for the traditional invasive tests and/or laboratory analyses, the systems and methods for predicting a wellness metric facilitate faster intelligent inference with a higher success rate.

Furthermore, the systems and methods for predicting a wellness metric entail use of machine learning/artificial intelligence to directly map the non-invasive parameters to predicted outcomes and/or wellness metrics. Moreover, the input set of non-invasive parameters may be advantageously expanded or modified based on the state-of-art, thereby facilitating further enhancement of the reliability of the predicted outcomes and/or wellness metrics as the systems and methods described herein are not tied down to a biological model and/or biological relationships.

Although specific features of embodiments of the present specification may be shown in and/or described with respect to some drawings and not in others, this is for convenience only. It is to be understood that the described features, structures, and/or characteristics may be combined and/or used interchangeably in any suitable manner in the various embodiments.

While only certain features of the present specification have been illustrated and described herein, many modifications and changes will occur to those skilled in the art. It is, therefore, to be understood that the present specification is intended to cover all such modifications and changes as fall within the true spirit of the invention.

What is claimed is:

1. A method (200) of predicting a wellness metric (208, 314, 612), the method (200) comprising:
    training a model (116, 410, 606) with a training data comprising a combination of non-invasive biological parameters and invasive biological parameters measured at each instance of time from each test user of a plurality of test users,
    wherein said combination is obtained from each test user at a plurality of instances,
    wherein said training data specifies that a corresponding invasive biological parameter is an output of said model associated with the corresponding non-invasive biological parameters of the combination as inputs, said corresponding invasive biological parameter representing a respective systemic condition,
    wherein upon said training, said model is operative to receive as input a set of non-invasive biological parameters and provide as output the corresponding invasive biological parameter representing the respective systemic condition according to said training data;
    applying, after said training, an energy signal to a first user to form a respective response representing a first non-invasive biological parameter comprised in said set of non-invasive parameters;
    receiving a set of non-invasive biological parameters (106, 404, 602), including said first non-invasive biological parameter of said first user (102); and
    providing the set of non-invasive biological parameters (106, 404, 602) as the set of parameters to the model to cause the model (116, 410, 606) to predict a first invasive biological parameter as a measure of a wellness metric (208, 314, 612), including chronic inflammation, said first invasive biological parameter (310, 608) and said wellness metric (208, 314, 612) representing a systemic condition in a body of the first user (102).

2. The method (200) of claim 1, wherein the output of the model (116, 410, 606) is a predicted value of the wellness metric (208, 314, 612).

3. The method (200) of claim 1, wherein the first invasive biological parameter is one of serum protein electrophoresis, creatinine reactive protein, and salivary cortisol in the body of the user (102).

4. The method (200) of claim 3, wherein the set of non-invasive biological parameters (106, 404, 602) comprises bioimpedance values corresponding to at least two frequencies, and wherein the bioimpedance values are obtained by applying electrical signals corresponding to said at least two frequencies across the tissue of the first user (102).

5. The method (200) of claim 4, wherein the set of non-invasive biological parameters (106, 404, 602) further comprises pulse rate, heart rate variability, skin temperature, images of tongue, nail, and eye, age, gender, height, weight, and menstrual cycle data.

6. A method (300) for predicting a wellness metric (314, 612) corresponding to a first user (102), the method (300) comprising:
obtaining a plurality of sets of non-invasive biological parameters (106, 404, 602) corresponding to a plurality of test users (102), wherein the plurality of sets of non-invasive biological parameters (106, 404, 602) is measured at each instance of time from each test user (102) of the plurality of test users (102), and wherein the plurality of sets of non-invasive biological parameters (106, 404, 602) is obtained from each test user at a plurality of instances;
obtaining a plurality of sets of invasive biological parameters (408) corresponding to the plurality of test users (102), wherein the plurality of sets of invasive biological parameters (408) is measured at each instance of time from each test user (102) of the plurality of test users (102), and wherein the plurality of sets of invasive biological parameters (408) is obtained from each test user at a plurality of instances;
optimizing model parameters of a neural network (402) based on the plurality of sets of non-invasive biological parameters (106, 404, 602) and the plurality of sets of invasive biological parameters (408);
training the neural network (402) to perform corresponding tasks (406, 604) to generate a plurality of task-specific models (116, 410, 606);
applying energy signals to the first user to receive (302) a set of non-invasive biological parameters (106, 404, 602) corresponding to the first user (102);
receiving (304) an input corresponding to one or more selected tasks (406, 604);
retrieving (306) at least one task-specific model (116, 410, 606) of said plurality of task specific models, corresponding to the one or more selected tasks (406, 604) based on the input, wherein each task-specific model is trained to receive as input a set of non-invasive biological parameters and provide as output a corresponding invasive biological parameter representing a respective systemic condition; and
predicting (308) an invasive biological parameter (310, 608) based on the set of non-invasive biological parameters (106, 404, 602) and the task-specific model (116, 410, 606), wherein the invasive biological parameter is a measure of the wellness metric (314, 612), including chronic inflammation,
said invasive biological parameter (310, 608) and said wellness metric (314, 612) representing a systemic condition in a body of the first user (102); and
providing (316) the invasive biological parameter to facilitate analysis.

7. The method (300) of claim 6, wherein said applying operates to acquire continuously, via a non-invasive biological parameter acquisition unit (104), the set of the non-invasive biological parameters (106, 404, 602), wherein the non-invasive biological parameter acquisition unit (104) has a wearable form factor (502, 522, 542).

8. The method (300) of claim 6, wherein the set of non-invasive biological parameters (106, 404, 602) corresponding to the first user (102) comprises an age, a gender, height, weight, bioimpedance values, a pulse rate, sweat, skin temperature, a tongue characterization, a face characterization, a skin characterization, a nail characterization, an eye characterization, or combinations thereof, wherein the invasive biological parameter (408) is one of a creatinine reactive protein value, a salivary cortisol value, or a serum protein electrophoresis value, and wherein the wellness metric (314, 612) comprises an acute inflammation, stress, or combinations thereof.

9. The method (300) of claim 8, wherein predicting (308) the outcome (310, 608) comprises processing (312, 610) the set of non-invasive biological parameters (106, 404, 602) based on the task-specific model (116, 410, 606) to perform at least one of continuously determining the wellness metric (314, 612) and continuously predicting one or more of a creatinine reactive protein value, a salivary cortisol value, and a serum protein electrophoresis value.

10. The method (300) of claim 9, further comprising generating one or more indicators (616, 704, 706, 708, 710, 722, 724, 726, 728, 732, 734, 736, 738) representative of the wellness metric (314, 612), wherein the one or more indicators (616, 704, 706, 708, 710, 722, 724, 726, 728, 732, 734, 736, 738) provide metrics corresponding to a state of one or more of the chronic inflammation, the acute inflammation, and the stress.

11. The method (300) of claim 10, wherein providing (316) the outcome (310, 608) comprises communicating one or more of the wellness metric (314, 612), the predicted values of the one or more invasive biological parameters (408), and the one or more indicators (616, 704, 706, 708, 710, 722, 724, 726, 728, 732, 734, 736, 738).

12. The method (300) of claim 11, further comprising visualizing one or more of the wellness metric (314, 612), the predicted values of the one or more invasive parameters (408), and the one or more indicators (616, 704, 706, 708, 710, 722, 724, 726, 728, 732, 734, 736, 738) on a display (120, 614, 702).

13. A system (100) for predicting a wellness metric (314, 612) corresponding to a first user (102), the system (100) comprising:
a plurality of task-specific models formed by:
obtaining a plurality of sets of non-invasive biological parameters (106, 404, 602) corresponding to a plurality of test users (102), wherein the plurality of sets of non-invasive biological parameters (106, 404, 602) is measured at each instance of time from each test user (102) of the plurality of test users (102), and wherein the plurality of sets of non-invasive biological parameters (106, 404, 602) is obtained from each test user at a plurality of instances;

obtaining a plurality of sets of invasive biological parameters (408) corresponding to the plurality of test users (102), wherein the plurality of sets of invasive biological parameters (408) is measured at each instance of time from each test user (102) of the plurality of test users (102), and wherein the plurality of sets of invasive biological parameters (408) is obtained from each test user at a plurality of instances;

optimizing model parameters of a neural network (402) based on the plurality of sets of non-invasive biological parameters (106, 404, 602) and the plurality of sets of invasive biological parameters (408);

training the neural network (402) to perform corresponding tasks (406, 604) to generate said plurality of task-specific models (116, 410, 606);

an acquisition subsystem (110) configured to obtain a set of non-invasive biological parameters (106, 404, 602) corresponding to the first user (102) by applying an energy signal to said first user;

a processing subsystem (112) in operative association with the acquisition subsystem (110) and comprising a prediction platform (114), wherein the prediction platform (114) is configured to:

receive the set of non-invasive biological parameters (106, 404, 602) corresponding to the first user (102);

receive an input corresponding to one or more selected tasks (406, 604);

retrieve at least one task-specific model (116, 410, 606) of said plurality of task-specific models corresponding to the one or more selected tasks (406, 604) based on the input;

predict an invasive biological parameter (310, 608) based on the set of non-invasive biological parameters (106, 404, 602) and the task-specific model (116, 410, 606), wherein the invasive biological parameter is a measure of the wellness metric (314, 612), said invasive biological parameter (310, 608) and said wellness metric (208, 314, 612) representing a systemic condition in a body of the first user (102); and an interface unit (120, 122) configured to provide the invasive biological parameter to facilitate analysis.

14. The system (100) of claim 13, wherein the task-specific model (116, 410, 606) is configured to predict at least one of a creatinine reactive protein value, a salivary cortisol value, and a serum protein electrophoresis value, determine a wellness metric, or a combination thereof.

15. The system (100) of claim 13, further comprises a non-invasive biological parameter acquisition unit (104) configured to acquire the set of the non-invasive biological parameters (106, 404, 602) corresponding to the first user (102), wherein the non-invasive biological parameter acquisition unit (104) has a wearable form factor (502, 522, 542).

16. The system (100) of claim 15, wherein the non-invasive biological parameter acquisition unit (104) comprises a wearable sock (502), a wearable glove (522), a wearable belt (542), or combinations thereof.

17. The system (100) of claim 16, wherein the wearable sock (502), the wearable glove (522), and the wearable belt (542) comprise one or more sensors (504, 506, 508, 524, 526, 528, 544, 546, 548) disposed thereon, and wherein the one or more sensors (504, 506, 508, 524, 526, 528, 544, 546, 548) are configured to acquire the one or more non-invasive biological parameters (106, 404, 602) corresponding to the first user (102).

18. The system (100) of claim 13, wherein the prediction platform (114) is further configured to:

generate one or more indicators (616, 704, 706, 708, 710, 722, 724, 726, 728, 732, 734, 736, 738) representative of the wellness metric (314, 612), and wherein the one or more indicators (616, 704, 706, 708, 710, 722, 724, 726, 728, 732, 734, 736, 738) provide metrics corresponding to a state of the wellness metric (314, 612); and provide the one or more indicators (616, 704, 706, 708, 710, 722, 724, 726, 728, 732, 734, 736, 738) corresponding to the wellness metric (314, 612) to facilitate further analysis or lifestyle recommendations.

19. A non-transitory computer readable medium that stores instructions executable by one or more processors to perform a method for predicting a wellness metric, comprising:

training a model (116, 410, 606) with a training data comprising a combination of non-invasive biological parameters and invasive biological parameters measured at each instance of time from each test user of a plurality of test users, said non-invasive biological parameters including bio-impedance, wherein said combination is obtained from each test user at a plurality of instances, wherein said training data specifies that a corresponding invasive biological parameter is an output of said model associated with the corresponding non-invasive biological parameters of the combination as inputs, said corresponding invasive biological parameter representing a respective systemic condition, wherein upon said training, said model is operative to receive as input a set of non-invasive biological parameters for a user and provide as output a corresponding invasive biological parameter representing a respective systemic condition in a body of the user;

applying, after said training, an energy signal to a first user to form a respective response representing said bio-impedance, receiving a set of non-invasive biological parameters (106, 404, 602), including said bio-impedance of said first user (102); and providing the set of non-invasive biological parameters (106, 404, 602) as the set of parameters to the model to cause the model (116, 410, 606) to predict said invasive biological parameter as a measure of a wellness metric (208, 314, 612), including chronic inflammation, for the first user (102).

20. The non-transitory computer readable medium of claim 19, wherein said method further comprises predicting a first invasive biological parameter by said model, and wherein said wellness metric is generated based on said first invasive biological parameter thereafter.

* * * * *